United States Patent
Battaglia

(10) Patent No.: US 12,257,344 B2
(45) Date of Patent: Mar. 25, 2025

(54) POLYMERSOMES FUNCTIONALISED WITH MULTIPLE LIGANDS

(71) Applicant: UCL BUSINESS LTD, London (GB)

(72) Inventor: Giuseppe Battaglia, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 17/419,937

(22) PCT Filed: Jan. 7, 2020

(86) PCT No.: PCT/GB2020/050026
§ 371 (c)(1),
(2) Date: Jun. 30, 2021

(87) PCT Pub. No.: WO2020/144467
PCT Pub. Date: Jul. 16, 2020

(65) Prior Publication Data
US 2022/0096382 A1    Mar. 31, 2022

(30) Foreign Application Priority Data

Jan. 7, 2019 (GB) ...................... 1900185

(51) Int. Cl.
| | |
|---|---|
| *A61K 9/1273* | (2025.01) |
| *A61K 47/62* | (2017.01) |
| *A61K 47/69* | (2017.01) |

(52) U.S. Cl.
CPC ........ *A61K 9/1273* (2013.01); *A61K 47/6907* (2017.08); *A61K 47/6915* (2017.08)

(58) Field of Classification Search
None
See application file for complete search history.

(56) References Cited

U.S. PATENT DOCUMENTS

| | | | |
|---|---|---|---|
| 6,384,105 B1 | 5/2002 | He et al. | |
| 7,229,973 B2 | 6/2007 | Bae et al. | |
| 10,357,454 B2 | 7/2019 | Kataoka et al. | |
| 2003/0223938 A1 | 12/2003 | Nagy et al. | |
| 2005/0163743 A1 | 7/2005 | Lewis et al. | |
| 2006/0105982 A1 | 5/2006 | Pardridge | |
| 2008/0181939 A1 | 7/2008 | Discher et al. | |
| 2008/0311045 A1 | 12/2008 | Hardy | |
| 2009/0060955 A1 | 3/2009 | Bae et al. | |
| 2009/0286247 A1 | 11/2009 | Hirao et al. | |
| 2010/0003336 A1 | 1/2010 | Deming et al. | |
| 2010/0226955 A1 | 9/2010 | Ludwig et al. | |
| 2010/0310660 A1 | 12/2010 | Tsai et al. | |
| 2010/0316706 A1 | 12/2010 | Joshi et al. | |
| 2011/0027347 A1 | 2/2011 | Bae et al. | |
| 2011/0065807 A1 | 3/2011 | Radovic-Moreno et al. | |
| 2011/0111036 A1 | 5/2011 | Lewis et al. | |
| 2011/0150941 A1 | 6/2011 | Battaglia | |
| 2011/0172240 A1 | 7/2011 | Milne et al. | |
| 2012/0076730 A1 | 3/2012 | Muro Galindo et al. | |
| 2012/0135070 A1 | 5/2012 | Kros et al. | |
| 2015/0079180 A1 | 3/2015 | Karaborni et al. | |
| 2015/0110713 A1 | 4/2015 | Manganaro et al. | |
| 2017/0020816 A1 | 1/2017 | Nagy et al. | |
| 2017/0202752 A1 | 7/2017 | Xu et al. | |
| 2019/0046445 A1 | 2/2019 | Battaglia | |
| 2019/0076359 A1 | 3/2019 | Battaglia | |
| 2021/0154142 A1 | 5/2021 | Battaglia et al. | |

FOREIGN PATENT DOCUMENTS

| | | |
|---|---|---|
| EP | 2 322 227 A1 | 5/2011 |
| JP | H03-31718 B2 | 5/1991 |
| JP | 2011-520841 A | 7/2011 |
| KR | 10-2017-0085784 A | 7/2017 |
| WO | 93/01221 A1 | 1/1993 |
| WO | 94/16749 A1 | 8/1994 |
| WO | 95/20407 A1 | 8/1995 |
| WO | 00/61114 A1 | 10/2000 |
| WO | 2001/082900 A1 | 8/2001 |
| WO | 02/028929 A1 | 4/2002 |
| WO | 03/074090 A2 | 9/2003 |
| WO | 2006/080849 A2 | 8/2006 |
| WO | 2009/061473 A2 | 5/2009 |

(Continued)

OTHER PUBLICATIONS

Lu F, Pang Z, Zhao J, Jin K, Li H, Pang Q, Zhang L, Pang Z. Angiopep-2-conjugated poly (ethylene glycol)-co-poly (ε-caprolactone) polymersomes for dual-targeting drug delivery to glioma in rats. International Journal of Nanomedicine. 2017;12:2117. (Year: 2017).*

Martín V, Herrera F, García-Santos G, Antolín I, Rodriguez-Blanco J, Rodriguez C. Signaling pathways involved in antioxidant control of glioma cell proliferation. Free Radical Biology and Medicine. Jun. 1, 2007;42(11):1715-22. (Year: 2007).*

Saul JM, Annapragada AV, Bellamkonda RV. A dual-ligand approach for enhancing targeting selectivity of therapeutic nanocarriers. Journal of controlled release. Sep. 12, 2006;114(3):277-87. (Year: 2006).*

Kluza E, Jacobs I, Hectors SJ, Mayo KH, Griffioen AW, Strijkers GJ, Nicolay K. Dual-targeting of αvβ3 and galectin-1 improves the specificity of paramagnetic/fluorescent liposomes to tumor endothelium in vivo. Journal of controlled release. Mar. 10, 2012;158(2):207-14. (Year: 2012).*

Nie Y, Schaffert D, Rödl W, Ogris M, Wagner E, Günther M. Dual-targeted polyplexes: one step towards a synthetic virus for cancer gene therapy. Journal of controlled release. May 30, 2011;152(1):127-34. (Year: 2011).*

(Continued)

*Primary Examiner* — Nissa M Westerberg
(74) *Attorney, Agent, or Firm* — Kilpatrick Townsend & Stockton LLP

(57) ABSTRACT

The present invention is directed to a nanoparticle or microparticle for binding to the surface of a cell, wherein the nanoparticle or microparticle comprises (i) multiple different ligand types on its external surface which are capable of binding to different respective receptor types on said cell surface, and (ii) a polymer brush on its external surface. The present invention is further directed to pharmaceutical compositions comprising a plurality of nanoparticles or microparticles of the invention, medical uses of such nanoparticles or microparticles, and a vaccine comprising such nanoparticles or microparticles.

7 Claims, 14 Drawing Sheets
Specification includes a Sequence Listing.

(56) References Cited

FOREIGN PATENT DOCUMENTS

| | | |
|---|---|---|
| WO | 2009/138472 A1 | 11/2009 |
| WO | 2009/138473 A2 | 11/2009 |
| WO | 2009/138477 A2 | 11/2009 |
| WO | 2010/124829 A1 | 11/2010 |
| WO | 2010/148653 A1 | 12/2010 |
| WO | 2011/005098 A1 | 1/2011 |
| WO | 2011/116132 A1 | 9/2011 |
| WO | 2012/046994 A2 | 4/2012 |
| WO | 2013/078562 A2 | 6/2013 |
| WO | 2014/122646 A1 | 8/2014 |
| WO | 2015/059180 A2 | 4/2015 |
| WO | 2015/153805 A2 | 8/2015 |
| WO | 2016/090111 A1 | 6/2016 |
| WO | 2017/144849 A1 | 8/2017 |
| WO | 2017/158382 A1 | 9/2017 |
| WO | 2017/191444 A1 | 11/2017 |
| WO | 2017/199023 A1 | 11/2017 |
| WO | 2017/218825 A1 | 12/2017 |
| WO | 2018/200951 A1 | 11/2018 |
| WO | 2019/197834 A1 | 10/2019 |

OTHER PUBLICATIONS

Liu Y, Hui Y, Ran R, Yang GZ, Wibowo D, Wang HF, Middelberg AP, Zhao CX. Synergetic combinations of dual-targeting ligands for enhanced in vitro and in vivo tumor targeting. Advanced healthcare materials. Aug. 2018;7(15):1800106. (Year: 2018).*
Mcclellan, Annie Katherine, "Raft Polymerization of Ph-Responsive, Diblock Copolymers for Nucleic Acid Delivery Vehicles" (2016). Electronic Theses and Dissertations. 398. (Year: 2016).*
Pardridge WM. Drug targeting to the brain. Pharmaceutical research. Sep. 2007;24:1733-44. (Year: 2007).*
Hucknall A, Rangarajan S, Chilkoti A. In pursuit of zero: polymer brushes that resist the adsorption of proteins. Advanced Materials. Jun. 19, 2009;21(23):2441-6. (Year: 2009).*
Abbas et al. "p21 in Cancer: Intricate Networks and Multiple Activities," (2009) Nat Rev. Cancer 9, 400-414.
Abdelmoshen et al. "Formation of Well-Defined, Functional Nanotubes via Osmotically induced Shape Transformation of Biodegradable Polymersomes," (2016) J. Am. Chem. Soc. 138, 9353-9356.
Anderson "Movement of a semipermeable vesicle through an osmotic gradient," (1983) Phys. Fluids 26, 2871-2879.
Arnold et al. "Enrichment of Single-Walled Carbon Nanotubes by Diameter in Density Gradients," (2005) Nano Letters 5, 713-718.
Arnold et al. "Sorting carbon nanotubes by electronic structure using density differentiation," (2006) Nature Nano 1, 60-65.
Bae et al. "Safety and Efficacy Evaluation of Carnosine, an Endogenous Neuroprotective Agent for Ischemic Stroke," (2013) Stroke, 44, 205-212.
Battaglia and Ryan "Bilayers and Interdigitation in Block Copolymer Vesicles," (2005) J. Am. Chem. Soc. 127(24), 8757-8764.
Battaglia and Ryan "Effect of Amphiphile Size on the Transformation from a Lyotropic Gel to a Vesicular Dispersion," (2006) Macromolecules 39, 798-805.
Battaglia and Ryan "Neuron-Like Tubular Membranes Made of Diblock Copolymer Amphiphiles," (2006) Angewandte Chemie International Edition 45(13), 2052-2056.
Battaglia and Ryan "Pathways of Polymeric Vesicle Formation," (2006) The Journal of Physical Chemistry B, 110, 102727-10279.
Battaglia and Ryan "The evolution of vesicles from bulk lamellar gels," (2005) Nat. Mater. 4, 869-876.
Battaglia et al. "Polymeric Vesicle Permeability: A Facile Chemical Assay," (2006), Langmuir 22, 4910.
Battaglia et al. "Wet Nanoscale Imaging and Testing of Polymersomes," (2011) Small 7(14), 2010-2015.
Battaglia G, Angioletti-Uberti S. Design principles for precision targeting. ChemRxiv. Cambridge: Cambridge Open Engage; Dec. 1, 2017; online preprint, DOI: 10.26434/chemrxiv.5647969.v1; 14 pages.
Battaglia G, Angioletti-Uberti S. Design principles for precision targeting. ChemRxiv. Cambridge: Cambridge Open Engage; Feb. 19, 2018; online preprint, DOI: 10.26434/chemrxiv.5647969.v2; 14 pages.
Tian X et al. On the design of precision nanomedicines. ChemRxiv. Cambridge: Cambridge Open Engage; May 22, 2019; online preprint, DOI: 10.26434/chemrxiv.5647969.v3; 34 pages.
Tian X et al. On the design of precision nanomedicines. ChemRxiv. Cambridge: Cambridge Open Engage; Nov. 12, 2019; online preprint, DOI: 10.26434/chemrxiv.5647969.v4; 27 pages.
Tian et al., "On the design of precision nanomedicines," Sci. Adv. 2020;6: eaat0919, 12 pages.
Bieging et al. "Unravelling mechanisms of p53-mediated tumour suppression," (2014) Nat. Rev. Cancer 14, 359-370.
Blanazs et al. "Mechanistic Insights for Block Copolymer Morphologies: How Do Worms Form Vesicles?," (2011) J. Am. Chem. Soc. 133(41), 16581-16587.
Blanazs et al. "Tailoring Macromolecular Expression at Polymersome Surfaces," (2009) Adv. Funct. Mater. 19(18), 2906-2914.
Canton et al. "Fully synthetic polymer vesicles for intracellular delivery of antibodies in live cells," (2013) FASEB J. 27(1), 98-108.
Canton et al. "Scavenger receptors in homeostasis and immunity," (2013) Nature Rev. Imm. 13, 621-634.
Cecchin et al. "Enzyme-driven chemotactic synthetic vesicles" (abstract and slides) presented at 248th ACS National Meeting: Stimuli-responsive supramolecular, macromolecular and nanostructured systems and biopolymer-driven organization of nanostructures (2014).
Chambon et al. "Facile Synthesis of Methacrylic ABC Triblock Copolymer Vesicles by RAFT Aqueous Dispersion Polymerization," (2012) Macromolecules 45, 5081-5090.
Chambon et al. "How Does Cross-Linking Affect the Stability of Block Copolymer Vesicles in the Presence of Surfactant?," (2012) Langmuir 28, 1196-120.
Chen et al. "High-Purity Separation of Gold Nanoparticle Dimers and Trimers," (2009) Journal of the American Chemical Society 131, 4218-4219.
Chen et al. "In vivo targeting of B-cell lymphoma with glycan ligands of CD22," (2010) Blood 115(23), 4778-4786.
Chen et al. "Polymersomes conjugated with des-octanoyl ghrelin and folate as a BBB-penetrating cancer cell-targeting delivery system," (2014) Biomaterials 35, 4066-4081.
Cheng and Deming, (2011) "Synthesis of Polypeptides by Ring-Opening Polymerization of α-Amino Acid N-Carboxyanhydrides" (. In: Deming T. (eds) Peptide-Based Materials. Topics in Current Chemistry, 310:1-26. Springer, Berlin.
Christian et al. "Spotted vesicles, striped micelles and Janus assemblies induced by ligand binding" (2009) Nature Mater 8, 843-849.
Colley et al. "Polymersome-Mediated Delivery of Combination Anticancer Therapy to Head and Neck Cancer Cells: 2D and 3D in Vitro Evaluation," (2014) Molecular Pharmaceuticals 11, 1176-1188.
Curk et al., "Optimal multivalent targeting of membranes with many distinct receptors," (2014) PNAS 114(28), 7210-7215.
Discher et al. "Polymersomes: Tough Vesicles Made from Diblock Copolymers," (1999) Science 284, 1143-1146.
Du et al. "pH-Sensitive Vesicles Based on a Biocompatible Zwitterionic Diblock Copolymer," (2005) J. Am. Chem. Soc 127(51), 17982-17983.
Ebbens et al. "Size dependence of the propulsion velocity for catalytic Janus-sphere swimmers," (2012) Phys. Rev. E 85 020401 (R).
Gaitzsch et al. "Synthetic Bio-nanoreactor: Mechanical and Chemical Control of Polymersome Membrane Permeability," (2012) Angew. Chem. Int. Ed. 51, 4448-4451.
Georgieva et al. "Peptide-Mediated Blood-Brain Barrier Transport of Polymersomes," (2012) Angew. Chem. Int. Ed. 51, 8339-8342.
Gerold et al. "Locking out hepatitis C," (2011) Nature Medicine 17, 542-544.
Ghoreschi et al. "Fumarates improve psoriasis and multiple sclerosis by inducing type II dendritic cells," (2011) J Exp Med 208, 2291-2303.

(56) References Cited

OTHER PUBLICATIONS

Giacomelli et al. "Phosphorylcholine-Based pH-Responsive Diblock Copolymer Micelles as Drug Delivery Vehicles: Light Scattering, Electron Microscopy, and Fluorescence Experiments," (2006) Biomacromolecules 7, 817-828.
Gordon "Osmophoresis," (1981) J Phys. Chem. 85, 1753-1755.
Grumelard et al. "Soft nanotubes from amphiphilic ABA triblock macromonomers," (2004) Chemical Communications 13, 1462-1463.
Joseph et al. "Chemotactic synthetic vesicles: Design and applications in blood-brain barrier crossing," (2017) Sci Adv 3, e1700362, 1-12.
Kim et al. "A Polymersome Nanoreactor with Controllable Permeability Induced by Stimuli-Responsive Block Copolymers," (2009) Adv Mat 21, 2787-2791.
Lagzi "Chemical robotics—chemotactic drug carriers," (2013) Central Eur J Medicine 8(4), 377-382.
Lee and Feihen "Polymersomes for drug delivery: Design, formation and characterization," (2012) J Control Release 161(2), 473-483.
Lillis et al. "The low density lipoprotein receptor-related protein 1: Unique tissue-specific functions revealed by selective gene knockout studies," Physiol Rev. Jul. 2008; 88(3): 887-918.
Linker et al. "Fumaric acid esters exert neuroprotective effects in neuroinflammation via activation of the Nrf2 antioxidant pathway," (2011) Brain 134, 678-692.
Liu et al. "Hydrolysable core crosslinked particles for receptor-mediated pH-sensitive anticancer drug delivery" (2015) New Journal of Chemistry 39(11), 8840-8847.
Loewe et al. "Nuclear Entry of NF-kB/p65 in Human Dimethylfumarate Inhibits TNF-Induced Endothelial Cells," (2002) J. Immunol. 168, 4781-4787.
Lomas et al. "Biomimetic pH Sensitive Polymersomes for Efficient DNA Encapsulation and Delivery," (2007) Adv. Mater. 19, 4238-4242.
Lomas et al. "Efficient Encapsulation of Plasmid DNA in pH-Sensitive PMPC-PDPA Polymersomes: Study of the Effect of PDPA Block Length on Copolymer-DNA Binding Affinity," (2010) Macromolecular Bioscience 10, 513-530.
Lomas et al. "Non-cytotoxic polymer vesicles for rapid and efficient intracellular delivery," (2008) Faraday discussions 193, 143-159.
Lopresti et al. "Controlling Polymersome Surface Topology at the Nanoscale by Membrane Confined Polymer/Polymer Phase Separation," (2011) ACS Nano 5(3), 1775-1784.
Lopresti et al. "Polymersomes: nature inspired nanometer sized compartments," (2009) J. Mater. Chem. 19, 3576-3590.
Martín et al. "Template Electrosynthesis of High-Performance Graphene Microengines," (2015) Small 11(29), 3568-3574.
Massignani et al "Controlling Cellular Uptake by Surface Chemistry, Size, and Surface Topology at the Nanoscale," (2009) Small 5(21), 2424-2432.
Massignani et al "Enhanced Fluorescence Imaging of Live Cells by Effective Cytosolic Delivery of Probes," (2010) Plos One, 5(5): e10459.
Meng et al. "Stimuli-Responsive Polymersomes for Programmed Drug Delivery," (2009) Biomacromolecules 10(2), 197-209.
Murdoch et al. "Internalization and biodistribution of polymersomes into oral squamous cell carcinoma cells in vitro and in vivo," (2010) Nanomedicine 5, 1025-1036.
Najafi et al. "Biodegradable micelles/polymersomes from fumaric/ sebacic acids and poly(ethylene glycol)," (2003) Biomaterials 24(7), 1175-1182.
Napoli et al., "Glucose-oxidase Based Self-Destructing Polymeric Vesicles," (2004) Langmuir 20(9), 3487-3491.
Neculai et al. "Structure of LIMP-2 provides functional insights with implications for SR-BI and CD36," (2013) Nature 504, 172-176.
Oltra et al. "From Stealthy Polymersomes and Filomicelles to Self Peptide-Nanoparticles for Cancer Therapy," (2014) Annu Rev Chem Biomol Eng 5, 281-299.
Paul et al. "Ring-opening copolymerization (ROCOP): synthesis and properties of polyesters and polycarbonates," (2015) Chem. Commun. 51, 6459-6479.
Pearson et al. "Effect of pH and Temperature on PMPC-PDPA Copolymer Self-Assembly," (2013) Macromolecules 46, 1400-1407.
Peng et al. "Self-Guided Supramolecular Cargo-Loaded Nanomotors with Chemotactic Behavior towards Cells," (2015) Angew Chem Int Ed 54, 11662-11665.
Pulicherla et al. "Targeting Therapeutics Across the Blood Brain Barrier (BBB), Prerequisite Towards Thrombolytic Therapy for Cerebrovascular Disorders—an Overview and Advancements," (2015) AAPS PharmSciTech 16(2), 223-233.
Reiner et al. "Optical manipulation of lipid and polymer nanotubes with optical tweezers," (2004) SPIE 5514, 246-253.
Reiner et al. "Stable and robust polymer nanotubes stretched from polymersomes," (2006) PNAS 103(5), 1173-1177.
Robertson et al. "pH-Sensitive Tubular Polymersomes: Formation and Applications in Cellular Delivery," (2014) ACS Nano 8(5), 4650-4661.
Robertson et al. "Purification of Nanoparticles by Size and Shape," (2016) Scientific Reports 6:27494.
Rosselgong et al. "Thiol-Functionalized Block Copolymer Vesicles," (2012) ACS Macro Letters 1, 1041-1045.
Ruiz-Perez et al. "Molecular engineering of polymersome surface topology," (2015) Sci Adv 2(4), e1500948).
Saha et al. "Clusters, asters, and collective oscillations in chemotactic colloids," (2014) Phys. Rev. E 89, 062316.
Sahari et al. "Directed transport of bacteria-based drug delivery vehicles: bacterial chemotaxis dominates particle shape," (2014) Biomedical Microdevices 16(5), 717-725.
Sanchez-Lopez et al. "Evaluation of liposome populations using a sucrose density gradient centrifugation approach coupled to a continuous flow system," (2009) Analytica Chimica Acta 645, 79-85.
Scannevin et al. "Fumarates Promote Cytoprotection of Central Nervous System Cells against Oxidative Stress via the Nuclear Factor (Erythroid-Derived 2)-Like 2 Pathway," (2012) J, Pharmacol. Exp. Ther. 341, 274-284.
Sharma et al. "Nanocarriers as Promising Drug Vehicles for the Management of Tuberculosis," (2013) Bionanoscience 3(2), 102-111.
Steineweg et al. "Fast and Cost-Effective Purifi cation of Gold Nanoparticles in the 20-250 nm Size Range by Continuous Density Gradient Centrifugation," (2011) Small 7(17), 2443-2448.
Sui et al. "Robust formation of biodegradable polymersomes by direct hydration," (2015) Polymer Chemistry 6(5), 691-696.
Sun et al. "Separation of Nanoparticles in a Density Gradient: FeCo@C and Gold Nanocrystals," (2008) Angewandte Chemie International Edition 48(5), 939-942.
Themistou et al. "Facile synthesis of thiol-functionalized amphiphilic polylactide-methacrylic diblock copolymers," (2014) Polymer Chem 5, 1405-1417.
Tian et al. "LRP-i.-mediated intracellular antibody delivery to the Central Nervous System," (2015) Scientific Reports 5:11990, 14 pages.
Van Oers et al. "Tubular Polymersomes: A Cross-Linker-Induced Shape Transformation," (2013) J. Am. Chem. Soc. 135(44), 16308-16311.
Vlieghe and Khrestchatisky "Peptide-based vectors for blood-brain barrier targeting and delivery of drugs to the central nervous system," (2010) Therapeutic Delivery 1(4), 489-494.
Wang et al. "Encapsulation of Biomacromolecules within Polymersomes by Electroporation," (2012) Angew. Chem., Int. Ed. 51, 11122-11125.
Xu et al. "Polymeric Micelles, a Promising Drug Delivery System to Enhance Bioavailability of Poorly Water-Soluble Drugs," (2013) J Drug Delivery ID 340315, 1-15.
Xu et al. "Thermosensitive Polypeptide Hydrogels as a Platform for ROS-Triggered Cargo Release with Innate Cytoprotective Ability under Oxidative Stress," (2015) Adv Healthcare Mat 5, 1979-1990.

(56) References Cited

OTHER PUBLICATIONS

Yakovlev and Deming "Controlled Synthesis of Phosphorylcholine Derivatives of Poly(serine) and Poly(homoserine)," (2015) J. Am. Chem. Soc. 137(12), 4078-4081.
Yealland et al. "Rescue of mitochondrial function in parkin-mutant fibroblasts using drug loaded PMPC-PDPA polymersomes and tubular polymersomes," (2016) Neuroscience Letters 630, 23-29.
Yu et al. "Targeting Strategies for Multifunctional Nanoparticles in Cancer Imaging and Therapy," (2012) Theranostics 2(1), 3-44.
Search Report issued by the UKIPO in respect of priority application No. GB1900185.8, dated Aug. 14, 2019, 4 pages.
Search Report and Written Opinion issued by the EPO in respect of international application publication No. WO 2020/144467, dated Mar. 19, 2020, 18 pages.
Chen et al., "Polymersomes conjugated with des-octanoyl ghrelin for the delivery of therapeutic and imaging agents into brain tissues", Biomaterials, vol. 35, Issue 6, pp. 2051-2065, Feb. 2014.

\* cited by examiner

POEGMA-PDPA/Angiopep

POEGMA-PDPA/PMPC

POEGMA-PDPA/PMPC + Angiopep

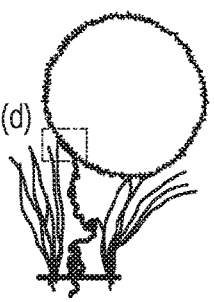
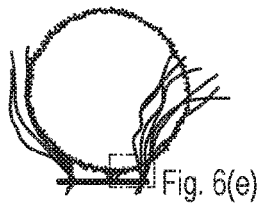
Fig. 6(d)
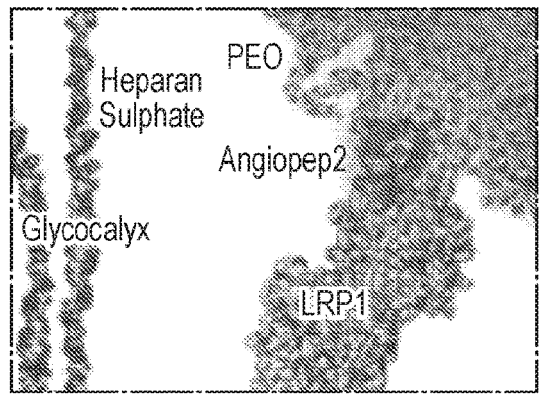
Fig. 6(e)
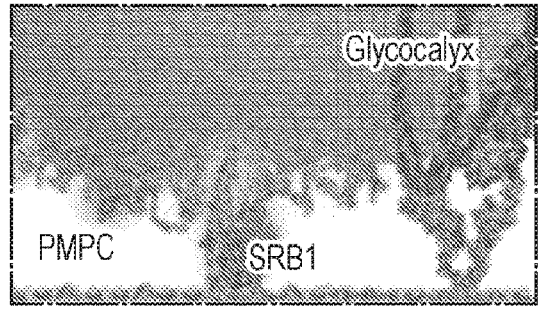

POLYMERSOMES FUNCTIONALISED WITH MULTIPLE LIGANDS

CROSS-REFERENCE TO RELATED APPLICATIONS

The present application is a national stage entry under 35 U.S.C. § 371 of International Patent Application No. PCT/GB2020/050026, filed Jan. 7, 2020, which claims priority to United Kingdom Application No. 1900185.8, filed Jan. 7, 2019, the disclosures of which are hereby incorporated by reference in their entirety for all purposes.

FIELD OF THE INVENTION

The present invention is directed to a nanoparticle or microparticle for binding to the surface of a cell, wherein the nanoparticle or microparticle comprises (i) multiple different ligand types on its external surface which are capable of binding to different respective receptor types on said cell surface, and (ii) a polymer brush on its external surface. The present invention is further directed to pharmaceutical compositions comprising a plurality of nanoparticles or microparticles of the invention, medical uses of such nanoparticles or microparticles, and a vaccine comprising such nanoparticles or microparticles.

BACKGROUND OF THE INVENTION

A key feature of effective small molecule therapy is the ability of a drug to interact with its biological target as selectively as possible, and indeed most drug discovery tools are refined to identify those molecules that bind with the highest affinity. Drug discovery today is now highly sophisticated and the advent of "-omic" technologies (such as genomics, transcriptomics, proteomics and metabolomics) has led to the possibility of personalised therapies (Aronson and Rehm, *Nature*, 2015, 526 (7573), 336-342). The ability to deliver drugs effectively to their site of action in vivo has also improved significantly in recent years. The high selectivity of active molecules can now therefore be combined with molecularly engineered carriers, such as nanoparticles or microparticles, equipped with the necessary attributes to navigate biological environments (Cheng et al., *Science*, 2012, 338 (6109), 903-910). A critical element of such a nanomedicinal effort is the introduction of ligands that enable targeting and selectivity to guide carriers across biological barriers. This technology has the potential to deliver drugs to target biological macromolecules that are not accessible via simple passive diffusion such as the inside of cells (Akinc and Battaglia, *Cold Harb Spring Perspect Biol*, 2013, 5(11), a016980) or the central nervous system (Fullstone et al., *Int Rev Neurobiol*, 2016, 130, 41-72).

Today, our ability to create ligands whether for drugging or simply targeting purposes is well advanced and can be extended to almost any biological unit. However, in most diseases, with cancer being the most exemplary one, the malfunction is associated with receptors that are endogenous and hence expressed by both healthy and diseased cells. Such a promiscuity is the major reason why many drugs are associated with undesirable side-effects and why many fail to advance through the clinical development pipeline. This is also often the reason why drug carriers may fail to deliver the drug to the required site of action and are instead adsorbed by the immune system. Such a situation requires an improvement in our ability to direct drugs to their intended target site.

It would therefore be desirable to provide medicaments that more effectively deliver the therapeutic agents to loci of interest, and in particular which enable high selectivity for one particular target site within a highly crowded environment where non-specific interactions are difficult to overcome. This would enable the same or a better therapeutic result to be achieved when using a lower dosing amount of the medicament, and/or the reduction of undesirable side effects. The present invention addresses these issues and provides improved medicaments for the therapeutic delivery of active agents to their intended sites of action.

SUMMARY OF THE INVENTION

The present invention addresses these problems via the provision of a multiplex nanoparticle or microparticle for binding to the surface of a cell, i.e. a nanoparticle or microparticle which comprises (i) multiple different ligand types on its external surface which are capable of binding to different respective receptor types on said cell surface, and (ii) a polymer brush on its external surface. It has surprisingly been found by the present inventors that nanoparticle- or microparticle-cell binding via multiple different ligand types results in enhanced selectivity in delivery of a drug cargo carried within the nanoparticle or microparticle, reducing undesired off-target binding. A further advantage of the present invention is that by using a multiplexed nanoparticle or microparticle, the cell surface receptors on a target cell (e.g. a cancer cell) are less readily able to mutate in such a fashion that would prevent effective binding of the nanoparticle or microparticle over time. This is particularly beneficial as the treatment courses for some diseases last a considerable amount of time (i.e. months or years). Furthermore, it is possible to predict the optimum number of each different ligand type on the surface of the nanoparticle or microparticle to enable optimum binding to the target cell surface.

In one aspect, the present invention accordingly provides a nanoparticle or microparticle for binding to the surface of a cell, wherein the nanoparticle or microparticle comprises at least a first ligand type on its external surface and at least a second ligand type on its external surface, wherein said first ligand type is capable of binding to a first receptor type on said cell surface, and said second ligand type is capable of binding to a second receptor type on said cell surface, further wherein the nanoparticle or microparticle comprises from 2 to 1000 ligands of the first ligand type and from 2 to 1000 ligands of the second ligand type. The nanoparticle or microparticle is typically a polymersome, liposome, synthosome or micelle, and it typically comprises a polymer brush on its external surface.

In a further aspect, the present invention provides a pharmaceutical composition comprising a plurality of the nanoparticles or microparticles according to the invention, and one or more pharmaceutically acceptable excipients or diluents.

In a yet further aspect, the present invention provides a nanoparticle or microparticle according to the invention, or a pharmaceutical composition according to the invention, for use in the treatment of a disease (e.g. cancer).

In a yet further aspect, the present invention provides a method of treating a cancer in a human patient, wherein said method comprises administration of a nanoparticle or microparticle according to the invention, or a pharmaceutical composition according to the invention, to a patient in need thereof.

In a yet further aspect, the present invention provides the use of a nanoparticle or microparticle according to the invention, or a pharmaceutical composition according to the invention, for the manufacture of a medicament for the treatment of a cancer in a patient.

In a yet further aspect, the present invention provides a vaccine comprising a nanoparticle or microparticle according to the invention and an antigen.

BRIEF DESCRIPTION OF THE FIGURES

FIGS. 6a-6g: Repulsive steric potentials. Schematics of the biding of a multivalent POEGMA-PDPA polymersome decorated with Angiopep peptide and targeting LRP1 (FIG. 6a) with PMPC chains and targeting SRB1 receptors (FIG. 6b) and with both ligands and targeting both receptors (FIG. 6c). The detail of the interaction between Angiopep and LRP1 (FIG. 6d) and PMPC and SRB1 (FIG. 6e) modulated by both the PEO and glycocalyx brushes. The corresponding repulsive steric potentials exerted on the LRP1 insertion in the PEO brush (FIG. 6f) and the polymersome inserting in the glycocalyx brush (FIG. 6g). These are calculated as a function of the polymersome radius, R and insertion parameter for the PEO chains, $\delta_P$, and for the glycocalyx heparan sulphate chains, $\delta_G$, respectively.

DETAILED DESCRIPTION

Nanoparticles and Microparticles

Figure 1A:
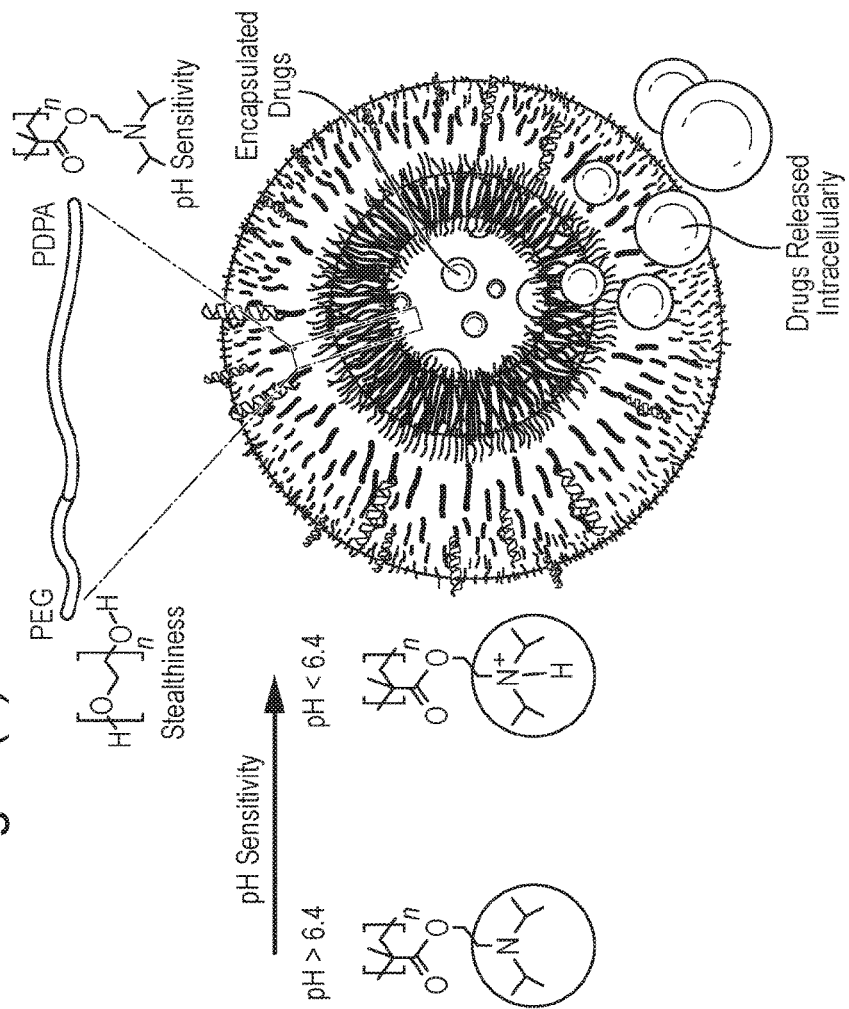
FIGS. 1a-1b: Theory of super-selectivity. Schematic diagram showing multiplexing ligand strategy on a polymersome scaffold (FIG. 1a) and ligand-receptor affinity curves for high-affinity monovalent ligands, low-affinity monovalent ligands, and multivalent ligands on a polymersome scaffold (FIG. 1b).

The nanoparticles and microparticles of the present invention can be any nanoparticles or microparticles suitable for delivery of a drug cargo to a target site of action in vivo. A "nanoparticle", as defined herein, is any particle between 1 and 100 nm in size. A "microparticle", as defined herein, is any particle between 0.1 and 100 μm in size. Suitable nanoparticles or microparticles for use in the present invention include polymersomes, liposomes, synthosomes, latex, micelles, nanocrystals, quantum dots, metallic nanoparticles, oxide nanoparticles, silica nanoparticles, protein cages, nano and micro gels, dendrimers, virus-like particles, protein, polymers or any other colloidal materials that fall within the aforementioned size range. Typically, however, the nanoparticles or microparticles for use in the present invention are polymersomes, liposomes, synthosomes or micelles. Typically, the nanoparticles or microparticles are self-assembled structures.

The nanoparticles and microparticles of the present invention may be of any feasible geometry, e.g. substantially spherical, ellipsoidal, cylindrical or bilayer form, but typically they are substantially spherical. A typical (largest) diameter of a nanoparticle or microparticle of the present invention is in the range 50 to 5000 nm. More typically, the diameter is in the range 50 to 1000 nm. Typically, the nanoparticles or microparticles of the present invention have a number average diameter of less than 300 nm, preferably less than 250 nm, most preferably less than 200 nm or 150 nm. In one aspect, the nanoparticle or microparticle of the present invention is a nanoparticle. Alternatively, the nanoparticle or microparticle of the present invention is a microparticle. Typically, particle size is measured using transmission electron microscopy (TEM). Typically, particle size distribution is measured using dynamic light scattering (DLS).

Preferably, the nanoparticle or microparticle of the invention is a polymersome. Polymersomes are synthetic vesicles formed from amphiphilic block copolymers. Examples of polymersomes are described in US 2010/0003336 A1, WO 2017/144849, WO 2017/158382, WO 2017/199023 and WO 2017/191444, the contents of each of which are herein incorporated by reference in their entirety. Over the last fifteen years they have attracted significant research attention as versatile carriers because of their colloidal stability, tuneable membrane properties and ability in encapsulating or integrating other molecules (for one representative review article, see *J Control Release* 2012 161(2) 473-83, the contents of which are herein incorporated by reference in their entirety).

Polymersomes are typically self-assembled structures. Polymersomes typically comprise an amphiphilic block copolymer, i.e. a block copolymer that comprises a hydrophilic block and a hydrophobic block. For example, the polymersome may comprise at least two such amphiphilic block copolymers, which are different from one another.

Such copolymers are able to mimic biological phospholipids. Molecular weights of these polymers are much higher than naturally-occurring phospholipid-based surfactants such that they can assemble into more entangled membranes (*J. Am. Chem. Soc.* 2005, 127, 8757, the contents of which are herein incorporated by reference in their entirety), providing a final structure with improved mechanical properties and colloidal stability. Furthermore, the flexible nature of the copolymer synthesis allows the application of different compositions and functionalities over a wide range of molecular weights and consequently of membrane thicknesses. Thus the use of these block copolymers as delivery vehicles offers significant advantages.

Polymersomes are often substantially spherical. Polymersomes typically comprise an amphiphilic membrane. The membrane is generally formed from two monolayers of amphiphilic molecules, which align and entangle to form an enclosed core with hydrophilic head groups facing the core and the exterior of the vesicle, and hydrophilic tail groups forming the interior of the membrane.

The thickness of the bilayer is generally between 2 and 100 nm, more typically between 2 and 50 nm (for instance between 5 and 20 nm). These dimensions can routinely be measured, for example by using Transmission Electron Microscopy (TEM) and/or and Small Angle X-ray Scattering (SAXS) (see, for example, *J. Am. Chem. Soc.* 2005, 127, 8757, the contents of which are herein incorporated by reference in their entirety).

When a polymersome is formed from more than one different type of copolymer, different regions of the polymersome typically have different bilayer thicknesses. For example, if a polymersome is formed from two different types of copolymer, preferably the thickness of the polymersome bilayer of a first region is from 1 to 10 nm, more preferably from 2 to 5 nm. Preferably the thickness of the polymersome bilayer of a second region is from 5 to 50 nm, for instance from 10 to 40 nm. More preferably the thickness of the polymersome bilayer of the second region is from 5 to 20 nm. Preferably the thickness of the polymersome bilayer of the first region is less than the thickness of the polymersome bilayer of the second region. Alternatively, the copolymers can have same thickness but different chemical compositions, which in turn create two different permeabilities with one copolymer forming a bilayer which is less permeable than the other.

In aqueous solution, normally an equilibrium exists between different types of structures, for instance between polymersomes and micelles. It is preferred that at least 80%, more preferably at least 90% or 95% by weight and most preferably all of the structures in solution are present as polymersomes. This can be achieved using the methods outlined herein.

It is known that when two different polymersome-forming copolymers are mixed to form a hybrid vesicle they phase-separate and thus give rise to polymersomes that contain discrete regions corresponding to the discrete copolymers. For example, this phenomenon is described in detail in *ACS NANO*, 5(3), 1775-1784 2011, the content of which is herein incorporated by reference in its entirety. Polymersomes can be readily manufactured by applying these known synthetic principles.

A polymersome is preferably capable of dissociating and releasing the encapsulated drug once it has reached the tissue of interest (i.e. the target tissue). Non-limiting, exemplary tissues of interest are discussed in more detail later and include cells (e.g. CNS cells) beyond the blood-brain barrier, immune cells and cancer cells. Preferably the polymersome is capable of dissociating and releasing the encapsulated drug after it has been internalised, via endocytosis, within a target cell (e.g. a CNS cell, an immune cell or a cancer cell).

Dissociation may be promoted by a variety of mechanisms, such as pH sensitivity of the block copolymer, thermal sensitivity of the block copolymer, hydrolysis (i.e. water sensitivity of the block copolymer) and/or redox sensitivity of the block copolymer.

The hydrophobic block of a copolymer comprised in the polymersome may also comprise pendant cationisable moieties as pendant groups. Cationisable moieties are, for instance, primary, secondary or tertiary amines as well as imidazole groups, capable of being protonated at pHs below a value in the range 3 to 6.9. Alternatively the group may be a phosphine.

Preferably, the hydrophobic block of the polymersome has a degree of polymerisation of at least 50, more preferably at least 70. Preferably, the degree of polymerisation of the hydrophobic block is no more than 250, even more preferably, no more than 200. Typically, the degree of polymerisation of the hydrophilic block is at least 10, preferably at least 15, and more preferably at least 20. It is preferred that the ratio of the degree of polymerisation of the hydrophilic to hydrophobic block is in the range 1:2.5 to 1:8. All of these limitations promote polymersome, rather than micelle formation.

The hydrophilic block may be based on condensation polymers, such as polyesters, polyamides, polyanhydrides, polyurethanes, polyethers (including polyalkylene glycols, especially polyethylene glycol (PEG)), polyimines, polypeptides, polypeptoids, polyureas, polyacetals and polysaccharides. Preferably, the hydrophilic block is based on a polymer selected from a poly(alkylene glycol), poly(vinyl pyrrolidone) (PVP), poly(2-methacryloyloxyethyl phosphorylcholine) (PMPC), poly(glycerol)s, poly(amino acid)s, polysarcosine, poly(2-oxazoline)s, poly[oligo(ethylene glycol) methyl methacrylate] and poly(N-(2-hydroxypropyl) methacrylamide). Most preferably, the hydrophilic block is based on PEG, poly(propylene glycol) or poly[oligo(ethylene glycol) methyl methacrylate]. The hydrophilic block may have zwitterionic pendant groups, in which case the zwitterionic pendant groups may be present in the monomers and remain unchanged in the polymerisation process. It is alternatively possible to derivatise a functional pendant group of a monomer to render it zwitterionic after polymerisation.

Polymersomes of the present invention may comprise any of the structural and/or functional features of the polymersomes described in any of WO 2017/144849, WO 2017/158382, WO 2017/199023 and WO 2017/191444, the contents of each of which are herein incorporated by reference in their entirety.

In one embodiment of this invention, the monomer from which the hydrophobic block is formed is 2-(diisopropylamino)ethyl methacrylate (DPA) or 2-(diethylamino)ethyl methacrylate (DEA).

In another embodiment, the hydrophobic block is formed from 2-(diisopropylamino)ethyl methacrylate (DPA) or 2-(diethylamino)ethyl methacrylate (DEA) and the hydrophilic block is based on a polyester, polyamide, polyanhydride, polyurethane, polyether, polyimine, polypeptide, polypeptoid, polyurea, polyacetal or polysaccharide. Preferably, the hydrophobic block is formed from 2-(diisopropylamino)ethyl methacrylate (DPA) or 2-(diethylamino) ethyl methacrylate (DEA) and the hydrophilic block is based on PEG, poly(propylene glycol) or poly[oligo(ethylene glycol) methyl methacrylate]. More preferably, a polymersome of the present invention comprises di-block PEG-PDPA, wherein PEG is poly(ethylene glycol), and the PDPA is poly(2-(diisopropylamino)ethyl methacrylate). Alternatively, a polymersome of the present invention comprises di-block POEGMA-PDPA, wherein POEGMA is poly[oligo(ethylene glycol) methyl methacrylate], and the PDPA is poly(2-(diisopropylamino)ethyl methacrylate). A particularly preferred diblock copolymer is $(P[(OEG)_{10}MA_{20}]$-$PDPA_{100})$. These copolymers have the ability to self-assemble in water or PBS and create vesicles having an aqueous lumen into which drugs can be loaded. The PEG functionality provides pendant hydroxyl groups, which act as handles for easy/reliable functionalisation of the polymers with ligands (as discussed below), while avoiding protein opsonization (giving polymersomes long circulation time and low unspecific binding). PDPA, meanwhile, is a pH-sensitive block that triggers the disassembly of polymersomes at pH values below 6.4, which is a typical pH during early stage endocytosis. The pH-sensitivity allows the drug payload to be released in the cell cytosol, upon internalization of the polymersome within a cell.

The block copolymer may be a simple A-B block copolymer, or may be an A-B-A or B-A-B block linear triblock copolymer or a $(A)_2B$ or $A(B)_2$ star copolymers (where A is the hydrophilic block and B is the hydrophobic block). It may also be an A-B-C, A-C-B or B-A-C block linear triblock copolymers or a ABC star copolymers (blocks linked together by the same end), where C is a different type of block. C blocks may, for instance, comprise functional, e.g. cross-linking or ionic groups, to allow for reactions of the copolymer, for instance in the novel compositions. Cross-linking reactions especially of A-C-B type copolymers, may confer useful stability on polymersomes. Cross-linking may be covalent, or sometimes, electrostatic in nature. Cross-linking may involve addition of a separate reagent to link functional groups, such as using a difunctional alkylating agent to link two amino groups. The block copolymer may alternatively be a star type molecule with hydrophilic or hydrophobic core, or may be a comb polymer having a hydrophilic backbone (block) and hydrophobic pendant blocks or vice versa. Such polymers may be formed for instance by the random copolymerisation of monounsaturated macromers and monomers.

Further details of a suitable process for polymerising the monomers are to be found in WO 03/074090, the contents of which are herein incorporated by reference in their entirety.

Exemplary methods that can be used for polymerising the monomers are atom-transfer radical polymerisation (ATRP) (see, e.g., an exemplary method described in Journal of the American Chemical Society 127, 17982-17983), living radical polymerisation process, functional NCA (N-carboxyanhydride) polymerisation with efficient postpolymerization modification and ring opening polymerisation (ROP). Living radical polymerisation has been found to provide polymers of monomers having a polydispersity (of molecular weight) of less than 1.5, as judged by gel permeation chromatography. Polydispersities in the range of from 1.2 to 1.4 for the or each block are preferred. The polymersomes may be loaded using a pH change system, electroporation or film hydration. In a pH change system process, polymer is dispersed in aqueous liquid in ionised form, in which it solubilises at relatively high concentrations without forming polymersomes. Subsequently the pH is changed such that some or all of the ionised groups become deprotonated so that they are in non-ionic form. At the second pH, the hydrophobicity of the block increases and polymersomes are formed spontaneously.

A method of forming polymersomes with an encapsulated material (e.g. an encapsulated drug) in the core may involve the following steps: (i) dispersing the amphiphilic copolymer in an aqueous medium; (ii) acidifying the composition formed in step (i); (iii) adding the material to be encapsulated to the acidified composition; and (iv) raising the pH to around neutral to encapsulate the material.

This method preferably comprises a preliminary step wherein the amphiphilic copolymer is dispersed in an organic solvent in a reaction vessel and the solvent is then evaporated to form a film on the inside of the reaction vessel.

Step (ii), of acidifying the composition, typically reduces the pH to a value below the pKa of the pendant group.

Another method of forming polymersomes with an encapsulated material in the core may involve the following steps: (i) dispersing the amphiphilic copolymer, and when needed the material to be encapsulated, in an organic solvent (e.g. a 2:1 chloroform:methanol mixture) in a reaction vessel; (ii) evaporating the solvent to form a film on the inside of the reaction vessel; and (iii) re-hydrating the film with an aqueous solution, optionally comprising a solubilised material to be encapsulated.

Another method of forming polymersomes with an encapsulated material in the core may involve the following steps: (i) dispersing the amphiphilic copolymer, and when needed the material to be encapsulated, in an organic solvent in a reaction vessel; (ii) adding the aqueous solvent to enable solvent switch and the formation of polymersomes on the inside of the reaction vessel; and (iii) optionally electroporating the obtained polymersomes to allow encapsulation of water-soluble bioactive molecules.

UV spectroscopy and HPLC chromatography may be used to calculate the encapsulation efficiency, using techniques well known in the art. An alternative method for forming polymersomes with an encapsulated material may involve simple electroporation of the material and polymer vesicles in water. For instance the drug may be contacted in solid form with an aqueous dispersion of polymer vesicles and an electric field applied to allow the formation of pores on the polymersomes membrane. The solubilised material molecules may then enter the polymersome vesicles though the pores. This is followed by membrane self-healing process with the consecutive entrapment of the material molecules inside the polymersomes.

Alternatively, material dissolved in organic solvent may be emulsified into an aqueous dispersion of polymer vesicles, whereby solvent and the material become incorporated into the core of the vesicles, followed by evaporation of solvent from the system.

The polymersomes used in the invention may be formed from two or more different block copolymers. In this embodiment, in the method of forming polymersomes, a mixture of the two or more block copolymers is used.

For example, 0.01% to 10% (w/w) of material to be encapsulated is mixed with copolymer in the methods described above.

Alternatively, the nanoparticle or microparticle of the present invention may be a liposome. A liposome is a spherical vesicle having at least one lipid bilayer. Typically, a liposome comprises a phospholipid, e.g. phosphatidylcholine, but may also include other lipids, such as egg phosphatidylethanolamine, so long as they are compatible with a lipid bilayer structure. The major types of liposomes include the multilamellar vesicle (MLLV, with several lamellar phase lipid bilayers), the small unilamellar liposome vesicle (SUV, with one lipid bilayer), the large unilamellar vesicle (LUV), and the cochleate vesicle.

Typically, the liposomes are fusogenic liposomes. This means that they are capable of fusing with a membrane, e.g. the cell surface membrane of a target cell, or the membrane of an endosome within the cell. Fusion of the bilayer of a fusogenic liposome with the cell surface membrane results in the incorporation of the liposome bilayer into the cell surface membrane, and the release of the drug cargo contained within the lysosome into the cell cytosol. Alternatively, the liposome may be internalized within a target cell via endocytosis, and the drug cargo carried within the liposome is released after fusion of the liposome bilayer with the endosomal membrane. The pH within an endosome is slightly acidic and therefore it is advantageous for the liposomes to be pH sensitive, e.g. the stability of the liposome structure is decreased at lower pH, facilitating fusion with the endosomal membrane. Other environments having low pH can also trigger the fusion of such liposomes, e.g., the low pH found in tumors or sites of inflammation.

Liposomes may be zwitterionic structures. Alternatively, liposomes may be amphoteric liposomes. This means that the liposomes have an isoelectric point and are negatively charged at higher pH values and positively charged at lower pH values. Typical pH-responsive elements in pH-sensitive liposomes include cholesterol hemisuccinate (CHEMS), palmitoylhomocysteine, dioleoylglycerol hemisuccinate (DOG-Succ) and the like.

Alternatively, the nanoparticle or microparticle of the present invention may be a synthosome. Synthosomes are a particular type of polymersome engineered to contain channels (transmembrane proteins) that selectively allow certain chemicals to pass through the membrane, into or out of the vesicle.

Alternatively, the nanoparticle or microparticle of the present invention may be a micelle. Micelles are aggregates (or supramolecular assemblies) of molecules having both hydrophilic and hydrophobic regions, dispersed in a liquid. Typically in an aqueous solution, the aggregated micelle is arranged such that the hydrophobic regions of the molecules are sequestered in the centre of the micelle, whilst the hydrophilic regions of the molecules present on the external surface of the micelle, and contact the aqueous solvent. Typically, micelles are substantially spherical in shape, although other shapes such as ellipsoid, cylindrical, torus and discoid are also possible.

Alternatively, the nanoparticle or microparticle of the present invention may be any object able to encapsulate and/or conjugate any type of bioactive molecules, such as anticancer drugs, proteins, peptides (natural or not), antibodies, fragment of antibodies, dyes, and the like.

Encapsulated Drug

The nanoparticle or microparticle of the present invention may comprise a drug encapsulated within the nanoparticle or microparticle. For the avoidance of doubt, it is also possible to encapsulate a plurality of different drugs within a single nanoparticle or microparticle, or to provide a plurality of nanoparticles or microparticles each containing a particular encapsulated drug.

As will be readily understood, the encapsulated drug is selected in accordance with the disorder to be treated. Non-limiting examples of such disorders are described elsewhere in this disclosure.

Non-limiting examples of drugs include: a drug that is effective for the treatment or prevention of a brain disorder; a drug that is effective for the treatment or prevention of the immune and/or inflammatory disorder; and a drug that is effective for the treatment or prevention of a cancer. There is no particular limitation on the identity of the drug and so drugs can be selected from those known in the art for treatment or prevention of the disorder of interest in any given embodiment.

Non-limiting examples of drugs include neuroprotectants, immunomodulatory drugs ("immunomodulators"), non-steroidal anti-inflammatory drugs (NSAIDs), corticosteroids, disease-modifying antirheumatic drugs (DMARDs) immunosuppressants, TNF-alpha inhibitors and anti-cancer drugs.

Illustrative and non-limiting examples of specific drugs that may be encapsulated include fumarate and fumarate esters, glutamate antagonists (e.g., Estrogen, Ginsenoside Rd, Progesterone, Simvastatin, Memantine), antioxidants (e.g., Acetylcysteine, Crocin, Fish oil, Minocycline, Pyrroloquinoline quinone (PQQ), Resveratrol, Vinpocetine, Vitamin E), Stimulants (e.g., Selegiline, Nicotine, Caffeine), Caspase inhibitors, Trophic factors (e.g., CNTF, IGF-1, VEGF, and BDNF), Anti protein aggregation agents (e.g. sodium 4-phenylbutyrate, trehalose, and polyQ-binding peptide), Erythropoietin, Lithium, carnosine, asiatic acid, flavonoids (e.g. xanthohumol, naringenin, galangin, fisetin and baicalin), cannabinoids (e.g., WIN55,212-2, JWH-133 and TAK-937), citicoline, minocycline, cerebrolysin, ginsenosoid-Rd, granulocyte-colony stimulating factor, Tat-NR2B9c, magnesium, albumin, paracetamol, aspirin, choline and magnesium salicylates, celecoxib, diclofenac (e.g. diclofenac potassium, diclofenac sodium), diflunisal, etodolac, fenoprofen, flurbiprofen, ibuprofen, indomethacin, ketoprofen, meclofenamate, mefenamic acid, meloxicam, nabumetone, naproxen (including naproxen sodium), oxaprozin, piroxicam, rofecoxib, salsalate, sodium salicylate, sulindac, tolmetin, valdecoxib, corticosteroids, alemtuzumab, interferon beta-1b, fingolimod, glatiramer acetate, natalizumab, plegridy, peginterferon beta 1a, teriflunomide, methotrexate, sulfasalazine, leflunomide, adalimumab, etanercept, golimumab, ustekinumab, azathioprine, cyclosporine, infliximab, golimumab, certolizumab, hydroxychloroquine, methotrexate, azathioprine, mycophenolate, acitretin, hydrea, isotretinoin, mycophenolate mofetil, sulfasalazine, 6-thioguanine, calcipotriol, calcitriol, tacalcitol, tacrolimus, pimecrolimus, dithranol, endamustine, bendamustine, carmustine, chlorambucil, cyclophosphamide, dacarbazine, ifosfamide, melphalan, procarbazine, streptozocin, temozolomide, capecitabine, 5-Fluoro Uracil, Fludarabine, Gemcitabin, Methotrexate, Pemetrexed, Raltitrexed, Actinomycin D, Bleomycin, Doxorubicin, Epirubicin, Mitomycin, Mitoxantrone, Etoposide, Docetaxel, Irinotecan, Paclitaxel, Topotecan, Vinblastine, Vincristine, Vinorelbine, Eribulin, Carboplatin, Cisplatin, Oxaliplatin, Afatinib, Aflibercept, BCG, Bevacizumab, Brentuximab, Cetuximab, Crizotinib, Denosumab, Erlotinib, Gefitinib, Imatinib, Interferon, Ipilimumab, Lapatinib, Panitumumab, Pertuzumab, Rituximab, Sunitinib, Sorafenib, Trastuzumab emtansine, Temsirolimus, Trastuzumab, Vemurafenib, Clodronate, Ibandronic acid, Pamidronate, Zolendronic acid, Anastrozole, Abiraterone, Bexarotene, Bicalutamide, Buserelin, Cyproterone, Degarelix, Exemestane, Flutamide, Folinic acid, Fulvestrant, Goserelin, Lanreotide, Lenalidomide, Letrozole, Leuprorelin, Medroxyprogesterone, Megestrol, Mesna, Octreotide, Stilboestrol, Tamoxifen and Thalidomide.

Targeting Ligands

The nanoparticle or microparticle comprises at least two different ligand types on its external surface. A "ligand" may also be referred to herein as a "targeting moiety". By "on its external surface" is meant that each ligand is located such that it is able to interact with its target (as opposed to being located at an inaccessible position that precludes interaction with the target, for example by being encapsulated within the nanoparticle or microparticle).

Typically, the nanoparticle or microparticle of the present invention is for binding to the surface of a cell, and comprises at least a first ligand type on its external surface and at least a second ligand type on its external surface, wherein said first ligand type is capable of binding to a first receptor type on said cell surface, and said second ligand type is capable of binding to a second receptor type on said cell surface. Typically, the nanoparticle or microparticle of the present invention comprises from two to seven different ligand types on its external surface, each of which is capable of binding to a complementary receptor type on the cell surface. Preferably, the nanoparticle or microparticle of the present invention comprises from two to six different ligand types on its external surface, more preferably from three to five different ligand types, and most preferably four different ligand types.

Without wishing to be bound by any particular theory, it is believed that the multiplexing of ligands on the surface of a nanoparticle or microparticle in this fashion confers the property of "super-selectivity" for the target cells.

Figure 1B:
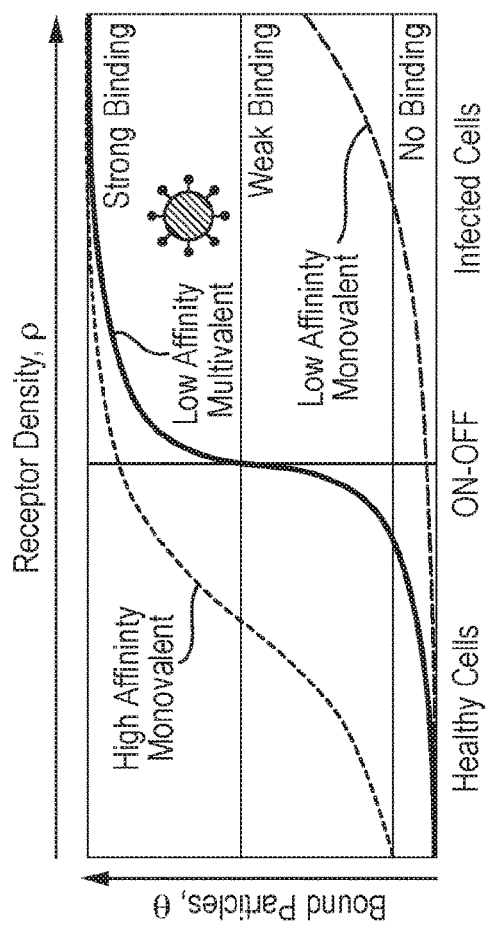
Figure 1B:
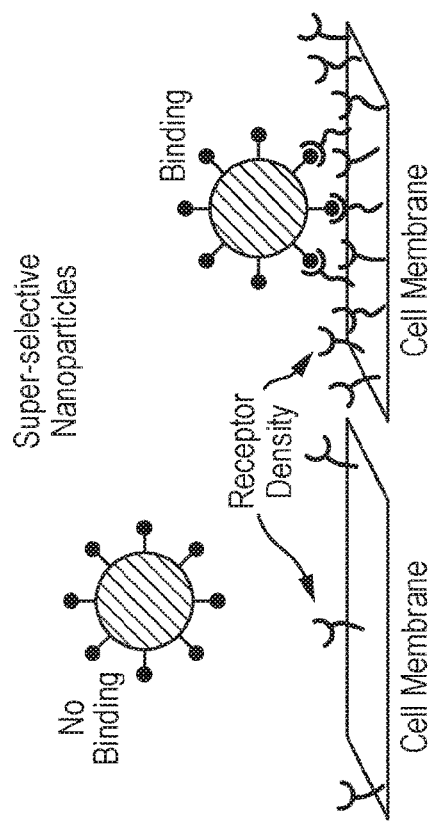

As shown in FIG. 1$b$, the probability to saturate receptors (i.e. bound particle fraction, $\theta$=1, FIG. 1$b$ right-hand side) for a monovalent ligand increases linearly with the number of receptors expressed on the cell membrane (p). This means that the stronger the affinity of the ligand-receptor binding, the stronger the ligand association. However, this means that if the ligand has a low affinity for its target receptor, a very high dose of ligand will be required to produce a response in the target (i.e. diseased) cells. Conversely, if the ligand has a high affinity for its target receptor, a large proportion of ligands will bind to any cells that express lower numbers of the targeted receptor (i.e. there will be undesired off-target effects).

However, if multiple ligands of the same type are confined on a nanoscopic scaffold such as a polymersome, the binding increases non-linearly with the receptor density following a sigmoidal function (FIG. 1$b$, green line). This corresponds to an "on-off" association, where binding only occurs above a given onset receptor density. Such a super-selective association enables the creation of nanoscopic or microscopic multiplexed polymersomes that target cell populations of interest more specifically. However, even these scaffolds suffer from some off-target effects, and require a medium to high level of receptor expression on the target cell surface.

Furthermore, relying on binding to only a single target receptor leaves open the possibility that the receptors on the target cell surface (e.g. that of a tumour cell) may mutate over time to evade binding to the nanoparticle/microparticle. The nanoparticles and microparticles of the present invention overcome these problems through the multiplexing of ligands on the surface of the scaffold (i.e. multiple different ligand types are present on the surface of the scaffold). This strategy is believed to further increase the selectivity of the nanoparticles/microparticles for their target cells, such that only very specific cell populations (i.e. diseased cells) are targeted, leaving the other (healthy) cells untouched.

For the super-selective interactions to be observed in the context of nanoparticles and microparticles, it is also advantageous that each ligand individually has a very low binding affinity for its target receptor. In practice, selective ligands with such a low binding energy to a target receptor are not readily available. The present inventors have discovered that this problem can be overcome by also providing on the surface of the nanoparticles or microparticles a moiety which creates an interference steric potential with the surface of the target cell, such as a polymer brush. Typically a polymer brush may comprise a naturally occurring polymer, such as a polypeptide or polysaccharide, or a synthetic polymer, such as any of the amphiphilic block copolymers described above. Components on the external surface of the target cell, such as glycans, glycoproteins and glycolipids (collectively referred to as the "glycocalyx"), are also believed to contribute to this repulsive steric potential.

Figure 2B:
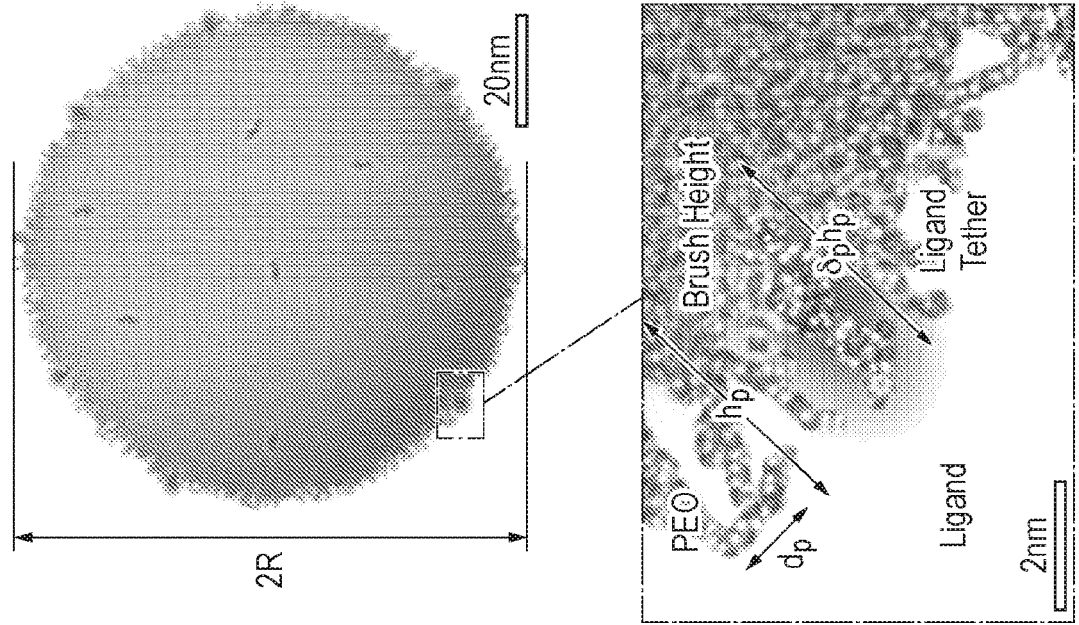
FIGS. 2a-2b: Examples of polymer brushes. Schematics of glycocalyx syndecan 4 and LRP1 receptor. Both proteins were reconstructed with atom resolution using computational methods and minimised for a brush conformation. The inset shows the details of the end part of the LRP1 next to the four heparan sulphate chains (FIG. 2a). Schematics of a POEGMA-PDPA polymersome decorated with Angiopep peptides. The polymersomes were reconstructed using minimised atomistic model of the single blocks which in turn have been assembled into a 50 nm vesicle (FIG. 2b). The inset detail shows that the peptide is well embedded in the polyethylene oxide (PEO) brush.
Figure 2A:
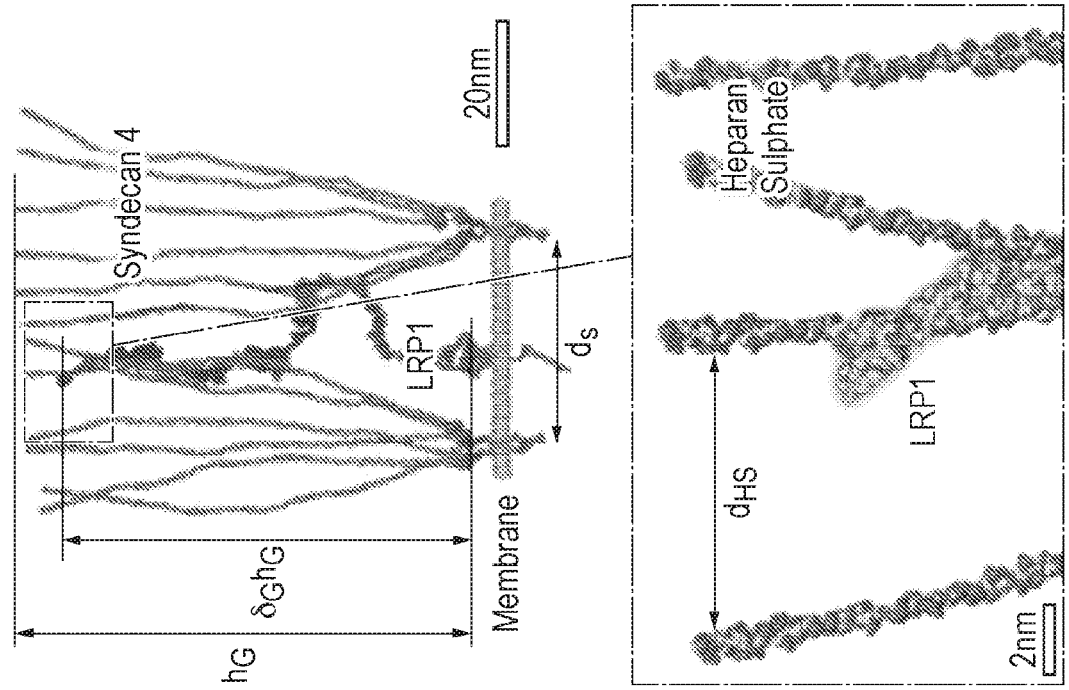

Preferred polymeric components of the polymer brush include poly(ethylene glycol) (PEG), poly(vinyl pyrrolidone) (PVP), poly(2-methacryloyloxyethyl phosphorylcholine) (PMPC), poly(glycerol)s, poly(sulfobetaine), poly(carboxybetaine), poly(amino acid)s, polysarcosine, poly(2-oxazoline)s, poly(N-(2-hydroxypropyl)methacrylamide), polyglycols, heparin, dextran, poly(ethylene glycol)-poly(2-(diisopropylamino)ethyl methacrylate) and/or poly(oligo (ethylene glycol) methyl ether methacrylate) (POEGMA). FIG. 2 illustrates some examples of polymer brushes on a cell surface (a) and on the external surface of a nanoparticle (b).

Preferably, the polymer brush has a degree of polymerisation of at least 5, more preferably at least 10. Preferably, the degree of polymerisation of the polymer brush is no more than 500, e.g. no more than 300, or no more than 200. Preferably, the polymer brush has a length of from 1.5 to 350 nm, and more preferably from 3 to 210 nm.

Hence, it is believed that polymersomes functionalized with two, or more, ligand types, each having relatively low affinity for their target receptor, can avoid targeting undesired cells, but still bind effectively to the target cells for drug delivery. Moreover, mutations in cell surface receptors will less likely lead to evasion of detection by the nanoparticles or microparticles. A schematic of the ligand binding strategy employed in the present invention is shown in FIG. 1$a$.

The number of each type of ligand on the external surface of the nanoparticle or microparticle is an important parameter in nanoparticle/microparticle design. The present inventors have discovered that the optimum number of ligands of each ligand type can be calculated in a very simple fashion once certain physical parameters of a ligand-receptor system are known. These relevant parameters can be readily determined by a person skilled in the art. Specifically, the optimum number of ligands of the $i^{th}$ ligand type (li) on the external surface of the nanoparticle or microparticle are defined according to the following equation (1):

$$\frac{\ln(a^{-1}-1)}{\ln(r_i e^{E_B(i)}+1)} + \frac{30 k_b T}{E_B(i)} \geq l_i \geq \frac{\ln(a^{-1}-1)}{\ln(r_i e^{E_B(i)}+1)} - \frac{30 k_b T}{E_B(i)} \quad (1)$$

wherein:
- a is the nanoparticle or microparticle activity and is calculated as $a=[P]V_P N_A$, wherein [P] is the molar concentration of nanoparticles or microparticles in bulk solution, $N_A$ is the Avogadro constant, and $V_P$ is the geometrical volume;
- $k_b$ is the Boltzmann constant;
- T is the absolute temperature;
- $E_B(i)$ is the total energy of binding of the $i^{th}$ ligand-receptor pair, given by the sum of (a) the ligand/receptor binding affinity $k_b T \ln K_D(i)$, wherein, $K_D(i)$ is the dissociation constant for the $i^{th}$ receptor/ligand couple, and (b) the steric interference, $E_s$, between the nanoparticle or microparticle and the cell surface; and
- $r_i$ is the density of receptors of type i on the cell surface.

This equation therefore provides a useful and novel empirical tool for determining the optimum number of each ligand type on the external surface of a nanoparticle or microparticle according to the present invention.

In the case of a spherical (or substantially spherical) particle, the parameter a can be calculated as $a=[P]N_A(\pi/3)[3(R+d)^3 - 2R^3]$, wherein R is the radius of the nanoparticle or microparticle, and d is the ligand tether length.

The number (and density) of each type of ligand on the external surface of a polymersome can typically be controlled during synthesis of the polymersome by varying the ratio of ligand-bound copolymer and "pristine" copolymer (i.e. diblock copolymer that does not have a ligand attached). For any given system, the number of ligands per polymersome is then given by the copolymer self-assembly parameter (related to the polymer molecular weight and the packing factor) and the polymersome size. The number of each type of ligand on the external surface of a polymersome (and hence the density of receptors) can typically be verified using mass spectrometry.

Typically, the ligand is attached to a polymer component on the external surface of the nanoparticle or microparticle. In the case of polymersomes, the ligand is typically attached to the hydrophilic block of the amphiphilic diblock copolymer. Thus, the ligand tether length d is given by the molecular mass of the hydrophilic block. Typically, d=0.3N nm, where N is the polymerisation degree of the hydrophilic block.

The overall steric potential $E_s$ is the sum of the steric potential arising from the glycocalyx brush on the cell surface and the steric potential arising from the polymer brush that coats the nanoparticle. The magnitude of both depends on how accessible the ligands and receptor are. This in turn depends on: (i) the relative height of the receptor with respect to the glycan/glycoprotein/glycolipid etc. chains on the cell surface ($\delta_G h_G$ where $h_G$ is the glycan/glycoprotein/glycolipid length and $\delta_G$ is between 0 and 1 and is a measure of how buried the receptor is in the glycocalyx), and (ii) the tether length of the ligands relative to the length of the polymer chains of the brush on the external surface of the nanoparticle ($\delta_P h_P$ where $h_P$ is the polymer chain length and $\delta_P$ is between 0 and 1 and is a measure of how buried the ligand is in the polymer brush). These parameters can readily be obtained for any given system from structural biology databases known in the art.

Typically, the nanoparticle or microparticle comprises from 2 to 1000 ligands of the first ligand type. Preferably, the nanoparticle or microparticle comprises from 5 to 1000 ligands of the first ligand type, more preferably from 10 to 500 ligands of the first ligand type, even more preferably from 20 to 200 ligands of the first ligand type, and most preferably from 50 to 100 ligands of the first ligand type.

Typically, the nanoparticle or microparticle comprises from 2 to 1000 ligands of the second ligand type. Preferably, the nanoparticle or microparticle comprises from 5 to 1000 ligands of the second ligand type, more preferably from 10 to 500 ligands of the second ligand type, even more preferably from 20 to 200 ligands of the second ligand type, and most preferably from 50 to 100 ligands of the second ligand type.

Typically, the nanoparticle or microparticle comprises from 2 to 1000 ligands of a subsequent (i.e. third or greater) ligand type. Preferably, the nanoparticle or microparticle comprises from 5 to 1000 ligands of the subsequent ligand type, more preferably from 10 to 500 ligands of the subsequent ligand type, even more preferably from 20 to 200 ligands of the subsequent ligand type, and most preferably from 50 to 100 ligands of the subsequent ligand type.

Typically, the combination of ligands on the surface of the nanoparticle or microparticle leads to a total binding energy of from 8 $k_B T$ to 30 $k_B T$, where $k_B$ is Boltzmann's constant and T is the temperature. This leads to on-off association profiles of the nanoparticles or microparticles wherein the receptors are saturated only above a given onset receptor density, whilst the nanoparticles or microparticles do not bind at all at lower receptor densities.

Each ligand type is adapted to enable the nanoparticle or microparticle to bind to a target. Typically the ligand binds selectively to the target. The target is a chemical substance that is located on or in the vicinity of the tissue of interest (and thus enables the nanoparticle or microparticle to accumulate specifically at the tissue of interest in preference to other sites). The target is preferably a receptor, e.g. a receptor that is present in particularly high quantity at the target tissue of interest. Most preferably, the target is a receptor on or within a cell surface membrane.

Each ligand type can be any ligand that binds specifically to the target. As is well known in the art, for example from the well-developed field of bioconjugates, a wide range of substances can be used as ligands, e.g. to target receptors.

In one embodiment, each ligand is a moiety that is attached to the external surface of the nanoparticle or microparticle. Examples of suitable ligands include antibodies, antibody fragments, aptamers, oligonucleotides, small molecules, peptides and carbohydrates. Peptide, protein, antibody and antibody fragment ligands are particularly preferred. However, any such moiety can be used as a ligand in the present invention. The suitability of any given moiety to target any given receptor can be determined using routine assay methods, involving testing for the ability of the moiety to bind specifically to the receptor.

One example of a ligand is a ligand that is adapted to enable the nanoparticle or microparticle to cross the blood-brain barrier (BBB). This property of the ligand arises through the ability of the ligand to bind to a target (e.g. a receptor) at the blood-brain barrier, wherein the target (e.g. receptor) mediates transcytosis across the blood-brain barrier.

Examples of receptors for receptor-mediated transcytosis that are highly expressed on the endothelial cells that form the blood-brain barrier include low-density lipoprotein receptor-related protein 1 (LRP-1), scavenger receptor class B, member 1 (SCARB1), insulin receptor (IR) and transferrin receptor 1 (TFRC), all of which are suitable targets for the targeting moiety.

In one embodiment, at least one of the ligand types, and preferably one ligand type, targets the LRP-1 receptor. LRP-1 is a member of the LDL receptor family that plays diverse roles in various biological processes including lipoprotein metabolism, degradation of proteases, activation of lysosomal enzymes and cellular entry of bacterial toxins and viruses. Deletion of the LRP-1 gene leads to lethality in mice, revealing a critical, but as of yet, undefined role in development. Tissue-specific gene deletion studies reveal an important contribution of LRP-1 in the vasculature, central nervous system, in macrophages and in adipocytes. Three important properties of LRP-1 dictate its diverse role in physiology: first, its ability to recognise more than thirty distinct ligands; second, its ability to bind a large number of cytoplasmic adaptor proteins via determinants located on its cytoplasmic domain in a phosphorylation-specific manner; and third, its ability to associate with and modulate the activity of other transmembrane receptors such as integrins and receptor tyrosine kinases.

It has been found that provision of a nanoparticle or microparticle that features a ligand that targets the LRP-1 receptor enables the nanoparticle or microparticle both to cross the BBB and to deliver efficiently an encapsulated drug into both the CNS parenchyma and CNS cells. In particular, it has been found that the endothelial transcytosis mechanism does not involve acidification of the nanoparticle or microparticle in membrane-trafficking organelles, which is important to avoid premature distintegration of the polymersome and concomitant release of the encapsulated drug. Still further, the LRP-1 receptor is associated with traditional endocytosis in CNS cells, which, subsequent to navigation across the BBB, aids the delivery of the drug within their cytosol (via disintegration of the nanoparticle or microparticle). In particular, providing a ligand that targets the LRP-1 receptor has been found to enable the nanoparticle or microparticle to achieve efficient neuroprotectant effects in the treatment of stroke.

Peptides that bind to the receptor LRP-1 are known in the art. For example, Angiochem (Montreal, Canada) have developed peptides that the leverage the LRP-1 mediated pathway to cross the blood-brain barrier when conjugated to drug cargos. One specific example of a peptide that is suitable for use in the present invention is Angiopep-2, which is a peptide having the sequence TFFYGGSRGKRNNFKTEEY (SEQ ID NO: 1). Further examples of suitable targeting moieties are disclosed in WO 2013/078562, the contents of which are herein incorporated by reference in their entirety (and, specifically, the ligand peptides disclosed in which are herein incorporated by reference).

In one embodiment, at least one of the ligand types, and preferably one ligand type, targets the SCARB1 receptor. The protein encoded by this gene is a plasma membrane receptor for high density lipoprotein cholesterol (HDL). The encoded protein mediates cholesterol transfer to and from HDL. In addition, this protein is a receptor for hepatitis C virus glycoprotein E2.

Malignant tumours display remarkable heterogeneity to the extent that even at the same tissue site different types of cells with varying genetic background may be found. In contrast, a relatively consistent marker the scavenger receptor type B1 (SR-B1) has been found to be consistently overexpressed by most tumour cells. Scavenger Receptor Class B Type I (SR-BI) is a high-density lipoprotein (HDL) receptor that facilitates the uptake of cholesterol esters from circulating lipoproteins. Additional findings suggest a critical role for SR-BI in cholesterol metabolism, signalling, motility, and proliferation of cancer cells and thus a potential major impact in carcinogenesis and metastasis. Recent findings indicate that the level of SR-BI expression correlate with aggressiveness and poor survival in breast and prostate cancer. Moreover, genomic data show that depending on the type of cancer, high or low SR-BI expression may promote poor survival. SR-BI is considered a diagnostic as well as prognostic indicator of cancer to help elucidate the contributions of this protein to cancer development, progression, and survival.

Ligands that bind to SCARB1 are known in the art. One such ligand is poly(2-(methacryloyloxy)ethyl phosphorylcholine) (PMPC).

Preferably, one ligand type on the nanoparticle or microparticle scaffold targets LRP-1 and another ligand type on the scaffold targets SCARB1.

In another embodiment, at least one of the ligand types, preferably one ligand type, is a ligand that is adapted to enable the nanoparticle or microparticle to bind to a cancer cell. Cancer cells typically have a high density of membrane receptors. Illustrative and non-limiting examples of such targeting moieties include proteins (mainly antibodies and their fragments), peptides, nucleic acids (aptamers), small molecules, vitamins and carbohydrates.

Examples of receptors for receptor-mediated transcytosis that are highly expressed on tumour cells include LRP-1, SCARB1, TFRC, folate receptor 1 (FOLR1) and epidermal growth factor receptor (EGFR). For example, SCARB1 is highly expressed in HeLa cells (cervical cancer) and FaDu cells (squamous cell carcinoma of the hypopharynx).

In one embodiment, at least one of the ligand types, and preferably one ligand type, targets LRP-1. In another embodiment, at least one of the ligand types, and preferably one ligand type, targets SCARB1. In another embodiment, at least one of the ligand types, and preferably one ligand type, targets TFRC. In another embodiment, at least one of the ligand types, and preferably one ligand type, targets FOLR1. In another embodiment, at least one of the ligand types, and preferably one ligand type, targets EGFR.

In one embodiment, at least one of the ligand types, and preferably one ligand type, targets the TFRC receptor. This gene encodes a cell surface receptor necessary for cellular iron uptake by the process of receptor-mediated endocytosis. This receptor is required for erythropoiesis and neurologic development.

Iron as an important element plays crucial roles in various physiological and pathological processes. Iron metabolism behaves in systemic and cellular two levels that usually are in balance conditions. The disorders of the iron metabolism balances relate with many kinds of diseases including Alzheimer's disease, osteoporosis and various cancers. In systemic iron metabolism that is regulated by hepcidin-ferroportin axis, plasma iron is bound with transferrin (TF) which has two high-affinity binding sites for ferric iron. The generic cellular iron metabolism consists of iron intake, utilization and efflux. During the iron intake process in generic cells, transferrin receptors (TFRs) act as the most important receptor mediated controls. TFR1 and TFR2 are two subtypes of TFRs those bind with iron-transferrin complex to facilitate iron into cells. TFR1 is ubiquitously expressed on the surfaces of generic cells, whereas TFR2 is specially expressed in liver cells. TFR1 has attracted more attention than TFR2 by having diverse functions in both invertebrates and vertebrates. Recently reports showed that TFR1 involved in many kinds of diseases including anemia, neurodegenerative diseases and cancers. Most importantly, TFR1 has been verified to be abnormally expressed in various cancers. Thus, TFR1 is postulated as a potential molecular target for diagnosis and treatment for cancer therapy.

In one embodiment, at least one of the ligand types, and preferably one ligand type, targets folate receptor 1 (FOLR1). The protein encoded by this gene is a member of the folate receptor family. Members of this gene family bind folic acid and its reduced derivatives, and transport 5-methyltetrahydrofolate into cells. This gene product is a secreted protein that either anchors to membranes via a glycosyl-phosphatidylinositol linkage or exists in a soluble form. Mutations in this gene have been associated with neurodegeneration due to cerebral folate transport deficiency.

The folate cycle sustains key metabolic reactions and is essential for rapidly growing cells. Under physiologic conditions, exogenous reduced folates (water-soluble B vitamins) are predominantly transported into cells via the low-affinity, high-capacity, ubiquitously expressed reduced folate carrier (RFC; bidirectional anion-exchange mechanism). Once in the cell, folates play an essential role in the biosynthesis of purines and thymidine, which in turn are required for DNA synthesis, methylation, and repair. Folates are also transported by high-affinity FRs. In humans, there are four isoforms of the FR (FRα, FRβ, FRγ, and FRδ). FRα, FRβ, and FRδ are attached to the cell surface by a glycosylphosphatidylinositol anchor, while FRγ is a secreted protein. Because FRα is expressed on the cell surface in a tumour-specific manner, it provides the potential to allow not only tumour localization, but also selected delivery of therapeutic agents to the malignant tissue, minimizing collateral toxic side-effects.

There are a number of unique advantages to exploiting FR as a diagnostic and therapeutic target. First, FRα is located on the luminal surface of epithelial cells in most proliferating nontumor tissues and is inaccessible to circulation. In contrast, FRα is expressed all over the cell in malignant tissue and is accessible via circulation. Second, FR has the ability to bind to folic acid, a relatively innocuous, small molecule that can rapidly penetrate solid tumours and is amenable to chemical conjugation with other molecules. Once a folate conjugate is bound to FR, it is internalized into the cell and the FRα is rapidly recycled to the cell surface via the FR-mediated endocytic pathway. These factors all emphasize the potential role of FRα in the diagnosis and treatment of specific tumour types.

In one embodiment, at least one of the ligand types, and preferably one ligand type, targets epidermal growth factor receptor (EGFR). The protein encoded by this gene is a transmembrane glycoprotein that is a member of the protein kinase superfamily. This protein is a receptor for members of the epidermal growth factor family. EGFR is a cell surface protein that binds to epidermal growth factor. Binding of the protein to a ligand induces receptor dimerization and tyrosine autophosphorylation and leads to cell proliferation.

Epidermal growth factor receptors (EGFRs) are a large family of receptor tyrosine kinases (TK) expressed in several types of cancer, including breast, lung, esophageal, and head and neck. EGFR and its family members are the major contributors of a complex signaling cascade that modulates growth, signaling, differentiation, adhesion, migration and survival of cancer cells. EGFR binds to its cognate ligand EGF, which further induces tyrosine phosphorylation and receptor dimerization with other family members leading to enhanced uncontrolled proliferation. Due to their multidimensional role in the progression of cancer, EGFR and its family members have emerged as attractive candidates for anti-cancer therapy.

Specifically, the aberrant activity of EGFR has shown to play a key role in the development and growth of tumor cells, where it is involved in numerous cellular responses including proliferation and apoptosis. The epidermal growth factor receptor (EGFR) signalling pathway is also a strong contender for both initiating and determining clinical outcomes in many respiratory diseases. Deregulation of the EGFR pathway causing aberrant EGFR signalling is associated with the early stage pathogenesis of lung fibrosis, cancer and numerous airway hypersecretory diseases, including COPD, asthma and cystic fibrosis.

Ligands for binding to each of these receptor are well known in the art. Example ligands for LRP-1 and SCARB1 are discussed above. Example ligands for TFRCs, e.g. TFR1, are transferrin and transferrin mimic peptide. An example ligand for FOLR1 is folic acid. An example ligand for EGFR is the peptide YHWYGYTPQNVI (SEQ ID NO: 2).

A further example of a ligand is a ligand that is adapted to enable the nanoparticle or microparticle to bind to an immune cell. Illustrative and non-limiting examples of such ligands include phosphorylcholine (as discussed in more detail below), peptidoglycan, lipoproteins, glycolipids, lipopolysaccharide, lipopeptides, synthetic compounds such as loxoribine and bropirimine, peptidoglycans, acetylated/malelylated proteins, modified low-density lipoproteins, polyanionic ligands, sulfated sugars, mannose-modified polysaccharides, fucose-modified polysaccharides, galactose-modified polysaccharides, proteins and β-glucan. In immune system cells targeting, the specific and precise targeting requires a particularly high level of discrimination/precision, which can be afforded by the nanoparticles and microparticles of the present invention.

Targeting of immune cells is believed to be important in treating immune-related diseases, such as autoimmune diseases and graft rejection, and for improving preventive/therapeutic vaccines. The cell membrane provides a remarkable example of spatiotemporal control of complex biological interactions thanks to hundreds of different ligands-receptors interactions selected trough evolution with the right amount of affinity and multi-combinatorial binding.

Packaging antigen and adjuvants into vehicles, such as polymersomes, can represent a major advantage. This approach allows for the vaccine carrier content to be protected from possible degradation and shielded from premature undesired receptor interaction, such as nucleic acids with scavenger receptors. Polymersomes are regarded a good choice for future vaccine formulations. Polymer particles may overcome the general stability issue of liposomes and, in contrast to virus-like particles, constitute non-immunogenic vehicles, which would allow for possible prime-boost regimens. Improved antigen processing and presentation as a result of co-localisation of antigen and stimulus in the same phagosome can explain why co-delivering antigen and adjuvant improves T-cell responses. At the same time, this approach ensures activation of the cells that have seen the antigen, which is crucial for efficient CD8+ T-cell priming. Major arguments in favour of co-targeting antigen and adjuvant lie in a more controlled vaccine application and in a reduced risk of adverse reactions, such as autoimmune responses, induction of tolerance, or unwanted systemic cytokine release.

This concept can be applied to several different pathologies, e.g. the incorporation of targeting ligands for targeting APC cells with applications in anti-cancer vaccines. A further example of a ligand is a ligand that is adapted to enable the nanoparticle or microparticle to bind to a neutrophil. Neutrophils are key effector cells in inflammation and play an important role in neutralizing invading pathogens. During inflammation resolution, neutrophils undergo apoptosis before they are removed by macrophages, but if apoptosis is delayed, neutrophils can cause extensive tissue damage and chronic disease. Promotion of neutrophil apoptosis is a potential therapeutic approach for treating persistent inflammation, yet neutrophils have proven difficult cells to manipulate experimentally.

Therapies that target components of the defence system such as neutrophils and neutrophil-associated effectors are promising for adjunct host-directed therapies to improve antibiotic efficacy, i.e. in tuberculosis treatment, and reduce both treatment time and long-term pathological sequelae.

Neutrophils have however proven very difficult cells to manipulate, and to the knowledge of the inventors, no commercially available vector exists that enables the efficient intracellular delivery of cargo within their short life span without compromising their viability and activation state.

Expression of high levels of immune cells including neutrophils has been associated with detrimental outcome in several solid tumours and new strategies to decrease their presence and activity are currently under clinical development. Accordingly, neutrophils are desirable targets for the nanoparticles and microparticles of the present invention.

A ligand can be attached to the external surface of the nanoparticle or microparticle using routine techniques, for example by adapting well known methods for attaching ligands to polymers, drugs, nucleic acids, antibodies and other substances. The attachment may be non-covalent (e.g. electrostatic) or covalent, though it is preferably covalent. For example, when the nanoparticle or microparticle is a polymersome, the targeting moiety can be attached by reacting a suitable functional group on the targeting moiety (including but not limited to an amine group, a carboxyl group and a thiol group) with a corresponding functional group on at least one of the copolymers that form, or will form, the polymersome. The attachment can be effected either before the polymersome structure is formed from the copolymers, or after the polymersomes have been formed.

In a particularly preferred embodiment, the nanoparticle or microparticle is a polymersome which comprises, on its external surface, a polymer brush comprising poly(ethylene glycol)-poly(2-(diisopropylamino)ethyl methacrylate) and each ligand type. Thus, the ligands are inserted in the polymer brush of polymersomes made of poly(ethylene glycol)-poly(2-(diisopropylamino)ethyl methacrylate), typically by employing a solvent-switch method. Typically, the density of the ligands within the brush can also be varied.

It is also possible to provide for attachment of the ligand to the copolymers by first chemically activating either or both of the ligand and the copolymers. For example, a peptide ligand may be activated by adding a reactive species to one of its termini, such as a cysteine moiety (whose thiol group is well known to react readily with functional groups such as the widely used maleimide moiety). Similarly, a copolymer can be activated by functionalising it with a reactive species (e.g. a maleimide moiety when the targeting moiety carries a thiol group). The copolymer may be provided with such a reactive species either by functionalisation of the copolymer itself, or by providing suitable monomers prior to the polymerisation that forms the copolymer, or by providing a suitable initiator for the polymerisation.

In a particularly preferred embodiment, the nanoparticle or microparticle is a polymersome wherein one or more ligands on the external surface of the polymersome are covalently bound to a poly(ethylene glycol) molecule. Tethering of the ligands to PEG molecules of different chain lengths in this way enables control over the deepness of the ligand insertion within the polymer brush. This in turn affects the steric repulsive potential, $E_s$, between the ligand and the target cell surface receptor. As discussed above, this steric potential is an important factor in determining the optimum number of ligands on the surface of the nanoparticle or microparticle for binding to a particular cell type.

A ligand may be attached directly to the external surface of the nanoparticle or microparticle, or alternatively it may be attached via a chemical spacer.

When the nanoparticle or microparticle is a polymersome, a ligand may also be a pendant group of a polymer comprised by the polymersome (i.e. at least one of the copolymers forming the polymersome itself). Clearly in this embodiment it is not necessary to undertake separate synthetic steps to attach the ligand to the copolymer or the resulting polymersome.

Suitable pendant groups generally include any group that corresponds to a ligand as defined elsewhere herein. In one illustrative embodiment, the targeting moiety is a phosphorylcholine moiety, i.e. a group having the formula

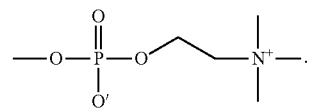

A phosphorylcholine moiety is a zwitterionic moiety that can constitute a pendant group in one or more of the monomers that form the copolymers comprised in a polymersome.

The phosphorylcholine moiety selectively targets scavenger receptor class B, member 1 (SCARB1) over-expressed by macrophages and other immune cells; in particular it enables a polymersome featuring phosphorylcholine moieties to enter such cells. Thus, polymersomes featuring a phosphorylcholine targeting moiety are particularly suitable for use in the treatment of inflammatory and/or immune disorders.

Pharmaceutical Compositions

The nanoparticle or microparticle of the present invention can be formulated as a pharmaceutical composition using routine techniques known in the art. For example, pharmaceutical compositions already utilised for the formulation of nanoparticles or microparticles such as polymersomes or drug-containing liposomes.

The pharmaceutical composition comprises a plurality of the nanoparticles or microparticles of the present invention. It also comprises one or more pharmaceutically acceptable excipients or diluents. The one or more pharmaceutically acceptable excipients or diluents may be any suitable excipients or diluents. The pharmaceutical composition is typically aqueous, i.e. it contains water (in particular sterile water).

A typical pH of the aqueous pharmaceutical composition is 7.0 to 7.6, preferably 7.2 to 7.4. Pharmaceutically acceptable buffers may be used to achieve the required pH. The pharmaceutical composition may be in the form of a sterile, aqueous, isotonic saline solutions.

Typically the pharmaceutical composition is an injectable composition, e.g. it is suitable for intravenous delivery, for example it is suitable for infusion.

Medical Uses of the Nanoparticles or Microparticles

The nanoparticles or microparticles of the present invention are able to target tissues including, but not limited to cells (e.g. CNS cells) beyond the blood-brain barrier, immune cells and cancer cells and to release drugs once localised at the target. As discussed above, the high efficiency in targeting emerges, at least in part, through the presence of multiple different ligand types (i.e. targeting moieties) on the external surface of the nanoparticle or microparticle (e.g. as part of the polymers themselves or as distinct moieties attached thereto).

Thus, the nanoparticles or microparticles of the present invention can be used in methods for the improved targeted treatment of diseases and other pathological conditions.

As will be readily understood, the ligands and encapsulated drug are selected in accordance with the disease to be treated. For example, if the disorder is a brain disorder then the ligands are ligands that are adapted to enable the nanoparticle or microparticle to cross the BBB and, typically, enter cells such as CNS cells beyond the BBB, while the drug is a drug that is effective for the treatment or prevention of the brain disorder. If the disorder is an immune and/or inflammatory disorder then the ligands may be ligands that are adapted to enable the nanoparticle or microparticle to bind to (and typically enter) an immune cell, while the drug is a drug that is effective for the treatment or prevention of the immune and/or inflammatory disorder. If the disorder is a cancer then the ligands may be ligands that are adapted to enable the nanoparticle or microparticle to bind to (and typically enter) a cancer cell, while the drug is a drug that is effective for the treatment or prevention of the cancer.

Examples of brain disorders include stroke, neurodegenerative diseases, traumatic brain injury (TBS), spinal cord injury, and neurotoxin consumption (for example, methamphetamine overdoses). Neurodegenerative diseases include conditions such as amyotrophic lateral sclerosis, Parkinson's disease, Alzheimer's disease and Huntington's disease. Stroke may be ischemic stroke or haemorrhagic stroke.

Examples of immune and/or inflammatory disorders include multiple sclerosis, psoriatic arthritis, rheumatoid arthritis, lupus erythematosus and psoriasis.

Examples of cancers include: cancers of the skin, such as melanoma; lymph node; breast; cervix; uterus; gastrointestinal tract; lung; ovary; prostate; colon; rectum; mouth; brain; head and neck; throat; testes; thyroid; kidney; pancreas; bone; spleen; liver; bladder; larynx; nasal passages; AIDS-related cancers; cancers of the blood and bone marrow, such as multiple myeloma and acute and chronic leukemias, for example, lymphoblastic, myelogenous, lymphocytic, and myelocytic leukemias; advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, eiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

Further disorders that may be susceptible to treatment or prevention with the nanoparticles or microparticles of the invention include HIV, atherosclerosis, ischemic heart disease and obstructive sleep apnoea.

Medical uses and methods of treatment, of course, involve the administration of a therapeutically effective amount of the nanoparticle or microparticle. A therapeutically effective amount of the nanoparticles or microparticles is administered to a patient. A typical dose is from 0.001 to 1000 mg, measured as a weight of the drug, according to the activity of the specific drug, the age, weight and conditions of the subject to be treated, the type and severity of the disease and the frequency and route of administration. Preferably, daily dosage levels are from 0.001 mg to 4000 mg.

The present invention further provides a method of treating or preventing a disorder that comprises administering a therapeutically effective amount of a nanoparticle or microparticle of the invention to a patient in need thereof. For example, the present invention provides a method of treating or preventing a disorder selected from any disorder specified in this disclosure, the drug being a drug that is capable of treating or preventing the said disorder, such as a brain disorder, an immune and/or inflammatory disorder, or a cancer. The present invention still further provides the use of a nanoparticle or microparticle of the present invention in the manufacture of a medicament for use in a method of treating or preventing a disorder as identified above.

The present invention further provides a vaccine comprising a nanoparticle or microparticle of the invention and an antigen. An antigen is any agent that causes the immune system of an animal body to produce an immune response, e.g. bacteria, viruses or pollen. Typically, the vaccine is administered to a human or animal recipient to induce the memory function of the adaptive immune system towards the specific antigen contained in the vaccine. Preferably, the nanoparticles or microparticles in the vaccine bind selectively to dendritic cells. Further preferably, the vaccine is a cancer vaccine.

EXAMPLES

The present invention is illustrated by the following examples. However, these examples do not limit the scope of the invention.

Example 1: Preparation of Polymersomes

Synthetic vesicles were made using amphiphilic copolymers made by poly(ethylene glycol) (PEG) as a hydrophobic block and poly(2-(diisopropylamino)ethyl methacrylate) (PDPA) as a hydrophilic block.

P[(OEG)$_{10}$MA]$_{20}$-PDPA$_{100}$, Cy5-P[(OEG)$_{10}$MA]$_{20}$-PDPA$_{100}$, Angiopep-P[(OEG)$_{10}$MA]$_{20}$-PDPA$_{100}$ and PMPC$_{25}$-PDPA$_{70}$ copolymers were synthesised as reported in Tian et al., *Sci Rep,* 2015, 5, 11990, the contents of which are incorporated herein by reference in their entirety.

The Angiopep-2 peptides on the surface of the polymersome target the LRP1 receptor and the PMPC ligands target the SCARB1 receptor. About 5% of the POEGMA-PDPA chains were labelled with Cy5 dye to allow fluorescence quantification. The Angiopep peptide was conjugated to POEGMA-PDPA copolymers and these were mixed at different concentration with pristine POEGMA-PDPA. The resulting arrangement of peptide expressed on the surface and immersed in the oligoethylene oxide chain ($N_p$=10) with a average interference parameter of $\delta_p$=0.8. The PMPC chains were co-polymerised with DPA to form PMPC$_{24}$-PDPA$_{70}$ and these were mixed with pristine POEGMA-PDPA chains at different concentrations.

To make 10 mg/mL polymersomes, the amount of copolymers was weighed and dissolved using pH 2 PBS. Once the film dissolved the pH was increased to 5.0. Peptide-functionalised copolymers were then added, in order to avoid acidic degradation. The pH was gradually increased to pH 6.8-7.0, eventually stopping at pH 7.4-7.5. Polymersomes formed during prolonged stirring at pH 6.8-7.0. The polymersomes were then ultrasound sonicated for 15-30 mins, at 4° C. The purification of polymersomes was finally performed by passing through a gel permeation chromatography column pre packed with Sepharose 4B (Sigma Aldrich). For long-term storage, the polymersomes can be kept at 4° C. and when conjugated to dyes are protected from light. The peptide-functionalised polymersomes were freshly made just before use. In this regard, it is important to note that although POEGMA-PDPA and PMPC-PDPA chains can undergo phase separation forming patchy polymersomes (see LoPresti et al., *ACS Nano,* 2011, 5(3), 1775-1784), the cellular experiments were performed right after preparation and hence without giving the sufficient time to separate (3-5 days).

Figure 3A:
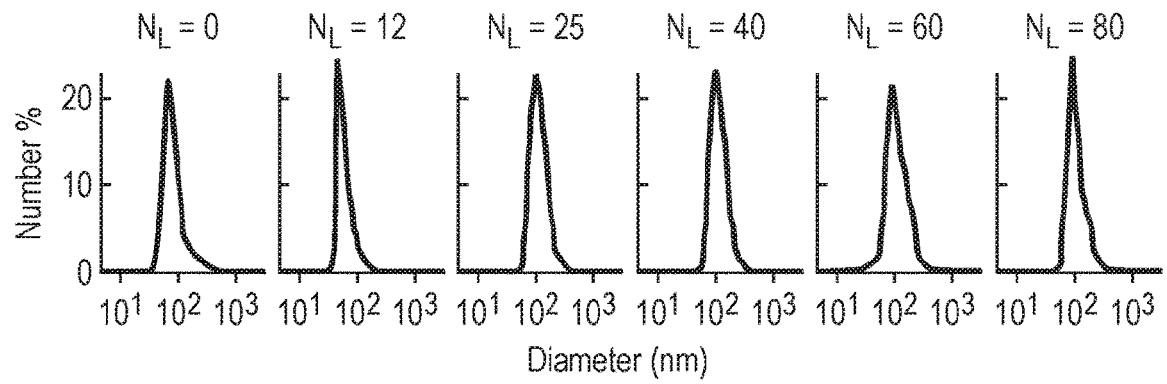
FIGS. 3a-3e: Polymersome characterisation. Particle size distributions measured by dynamic light scattering for POEGMA-PDPA/Angiopep (FIG. 3a), POEGMA-PDPA/PMPC (FIG. 3b) and POEGMA-PDPA/PMPC+Angiopep (FIG. 3c) polymersomes. Representative transmission electron micrographs of POEGMA-PDPA/Angiopep (25 ligands) (FIG. 3d) and POEGMA-PDPA/PMPC (1000 ligands) (FIG. 3e) formulations.
Figure 3B:
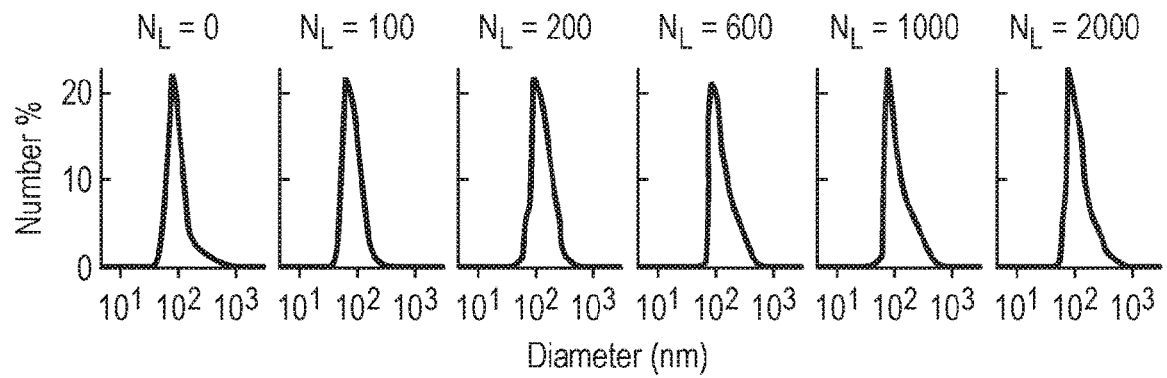
Figure 3C:
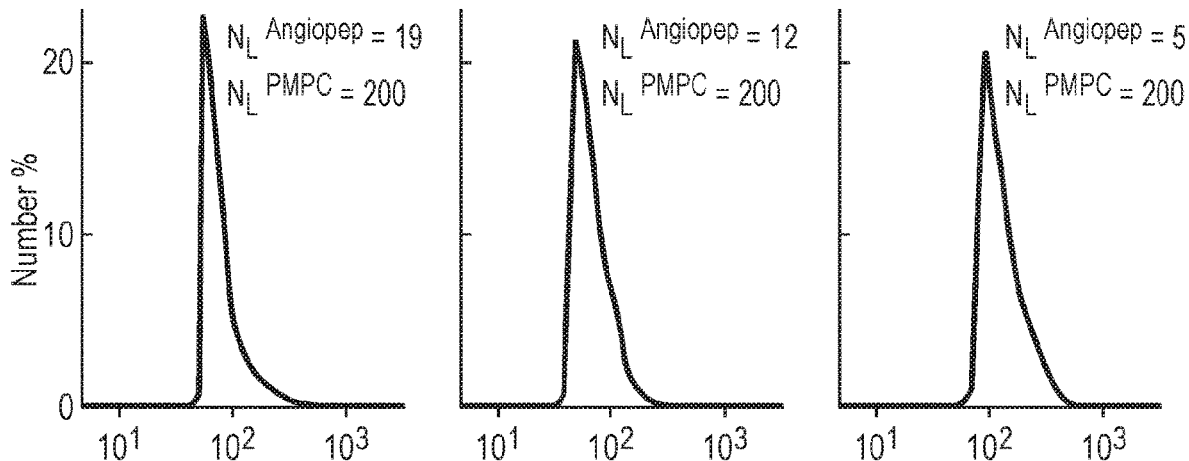
Figure 3D:
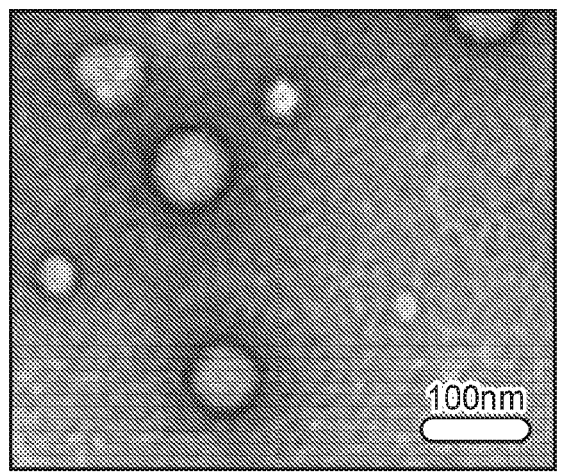
Figure 3E:
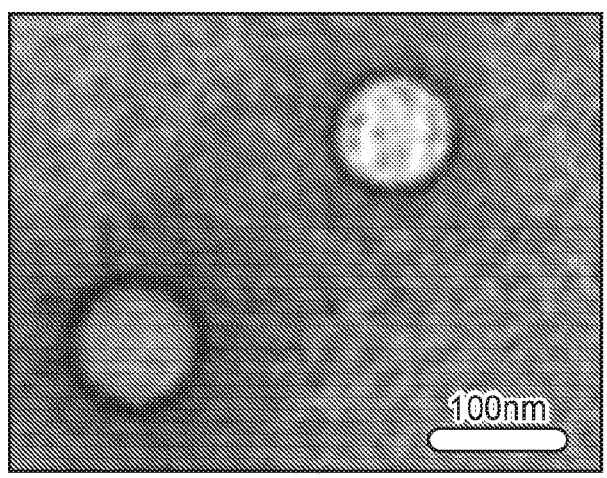

The particle size distribution of the polymersomes was measured via dynamic light scattering (DLS) (see FIGS. 3a-3c). All the formulations had an average radius of 50 nm (+/−10 nm) and the addition of the ligand did not alter the final structure as confirmed by both TEM and DLS. The polymersomes were further characterised by transmission electron microscopy (FEI Tecnai G2) using phosphotungstenic acid as staining agent and dynamic light scattering (Malvern Nanosizer) (see FIGS. 3d and 3e).

Example 2: Binding of Polymersomes to Brain Endothelial Cells

Brain endothelial bEND.3 cells (ATCC CRL-2299) were seeded on a rat-tail collagen Type I (Sigma Aldrich, C3867) pre-coated T-75 flask maintained in DMEM medium (Dulbecco's Modified Eagle's Medium-high glucose, D5671-Sigma) supplemented with 2 mM L-glutamine, 100 IU/mL penicillin, 100 mg/ml streptomycin, and 10% fetal calf serum (FCS). Cultures were maintained at 37° C. in an atmosphere of 5% CO$_2$ and 95% air and sub-cultured routinely using 0.02% (w/v) EDTA trypsin (5 mL, 5 min 37° C., 5% CO$_2$ incubation) once 100% confluence was reached. LADMAC macrophages were purchased from the American Type Culture Collection (Manassas, VA, USA) are were cultured in Eagle's minimal essential medium (EMEM) supplemented with 10% (v/v) FCS and 2 mM L-glutamine.

Cells were placed on 96-well plates with image-read bottom plastic, and treated for 1 hr with the different polymersomes formulations. Subsequently their media was replenished. Short incubation times were selected to ensure the nanoparticle/cell interaction was kinetically controlled by the binding, and whilst endocytosis might occur this accounts only for a negligible component of the overall process. The cells were imaged using confocal laser scanning microscopy equipped with an incubation chamber connected to ZEISS temperature control unit 37-2 and CO$_2$ controller. (Stabilisation of the temperature and CO$_2$ concentration was carried out for 1-2 hours before the experiment.) Confocal laser scanning microscopy was performed on a ZEISS LSM 510 microscope, equipped with the following lasers: Ar laser, 30 mW; HeNe laser, 1 mW and HeNe laser, 5 mW. The laser excitation wavelengths used were: 405 nm (DAPI), and 548 nm (Cy5-Polymersomes). The quantification of the fluorescence intensity was performed on 30 micrographs per formulation in triplicate. The images were analysed by ImageJ by creating an ad hoc region of interest around the nuclei (pre-stained with DAPI) and measuring the intensity in the Cy5 channel.

Figure 4A:
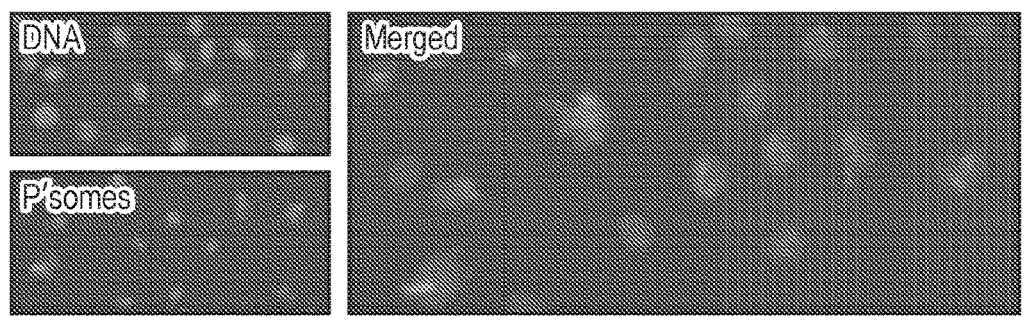
FIGS. 4a-4c: Selective cellular uptake. Example of Angiopep-polymersomes binding to brain endothelial cells after 1 hr incubation (FIG. 4a). The cell DNA was stained by DAPI dye (upper left) and the polymersomes are labelled by Cy5 dyes (lower left). The average fluorescence per cell measured after 1 hr incubation of polymersomes with brain endothelial cells (line A), lymphocytes and macrophages (line B) as a function of ligand numbers for the Angiopep peptides (FIG. 4b) and PMPC chains (FIG. 4c). The line C shows the selectivity index calculated using the brain endothelial cells as target and the macrophages as sentinel cells.
Figure 4B:
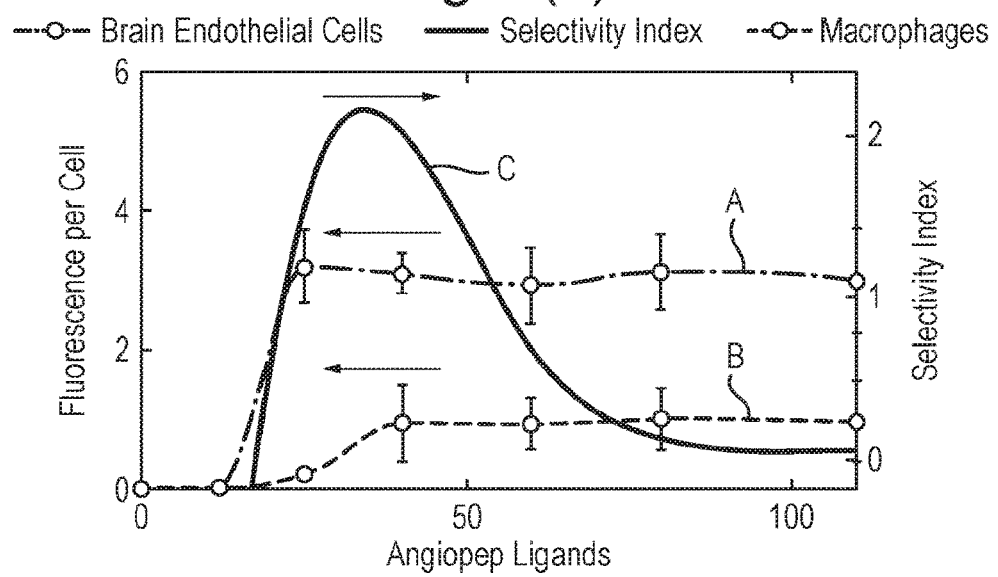
Figure 4C:
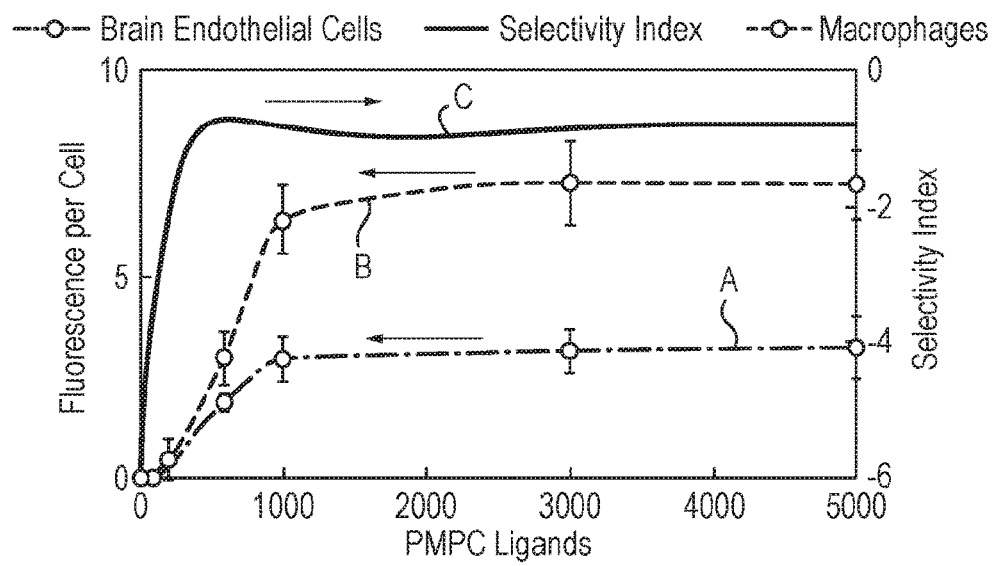

The results are shown in FIG. 4. In FIG. 4a, an example of micrograph used for quantification is shown to illustrate the effective binding of ligand-modified polymersomes to brain endothelial cells. FIGS. 4b and 4c meanwhile show the average fluorescence per cell measured after 1 hr incubation with brain endothelial cells, macrophages and lymphocytes. To assess the ability of polymersomes to selectively target a given cell phenotype, a parameter known as the selectivity index, s, can be defined as:

$$s = \log \frac{F_{BE}^2}{\max(F_{BE})F_S}$$

wherein $F_{BE}$ is the average fluorescence per cell in brain endothelial cells (i.e. the target cells), and $F_S$ is the average fluorescence per cell in either the lymphocyte or macrophage cells (herein considered as sentinel cells). Formulations with s>1 interact preferentially with target cells than the sentinel cells, whilst formulations with s<0 interact preferentially with the sentinel cells, and formulations with 1≥s≥0 are indiscriminate and do not bind with high selectivity to either target or sentinel cells.

As shown in FIG. 4b, the Angiopep-decorated polymersomes interact preferentially with brain endothelial cells compared to the two sentinel cell types, with selectivity peaking at 2.5 when around 30 ligands are present. As expected at a higher ligand number, the selectivity is lost and the polymersomes interact equally with all cell populations.

A very different outcome is observed for PMPC-decorated chains, for which the macrophages show the highest uptake, followed by the lymphocytes and finally the brain endothelial cells (albeit the fluorescence output in the brain endothelial cells is of a similar magnitude to that observed with the Angiopep polymersomes). Here the selectivity is negative with regard to the brain endothelial cells.

Figure 5:
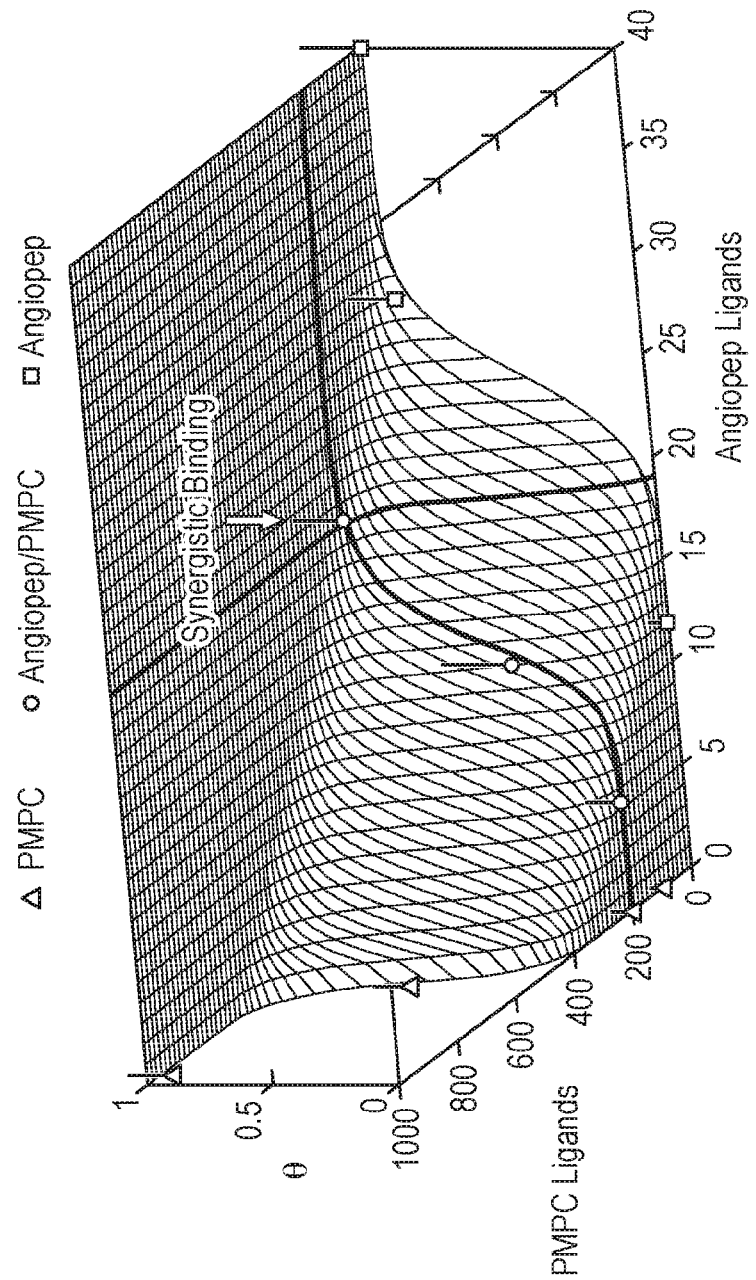
FIG. 5: Super-selectivity validation on brain endothelial cells. Plot to show binding of multiplexing polymersomes decorated with both Angiopep peptides and PMPC chains to brain endothelial cells.
Figure 6A:
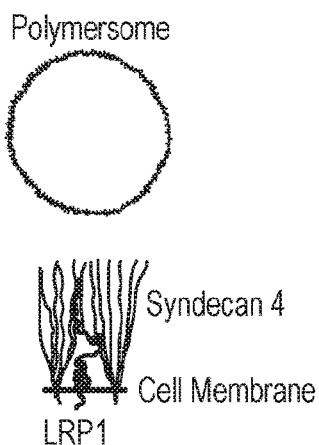
Figure 6B:
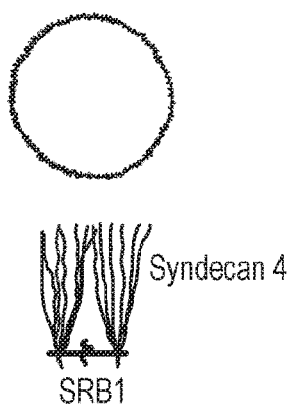
Figure 6C:
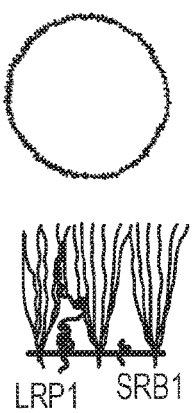
Figure 6F:
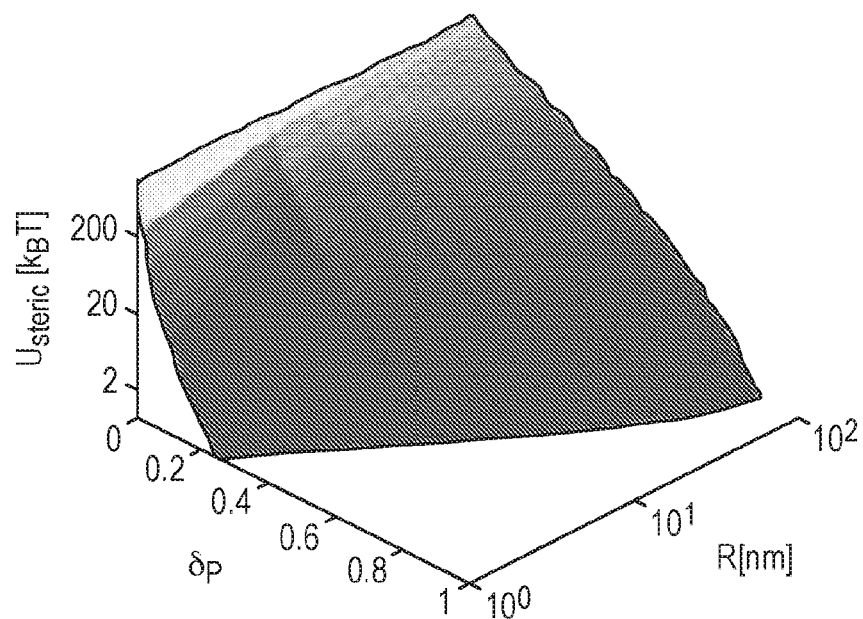
Figure 6G:
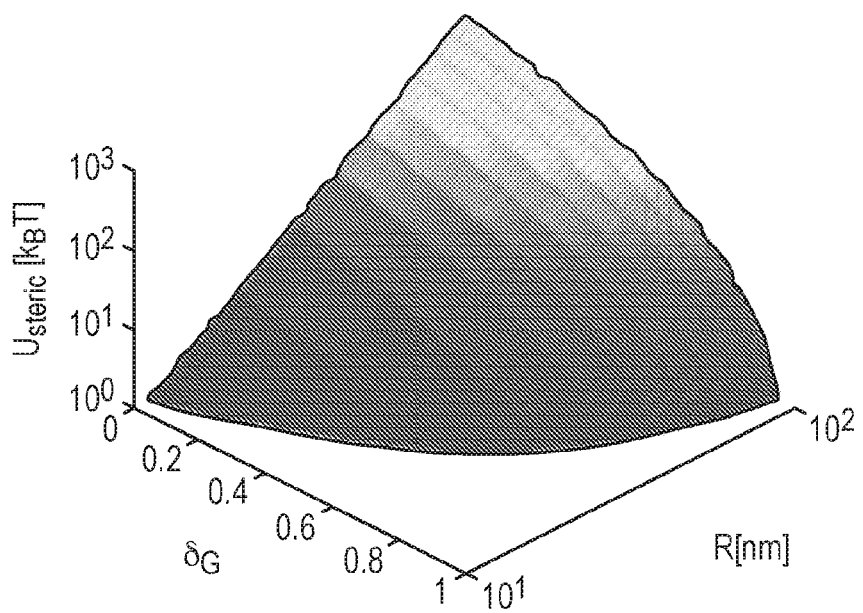

Three PEG-PDPA polymersomes with both Angiopep and PMPC ligands expressed were also synthesised and incubated with brain endothelial cells. The results are plotted in FIG. 5. These show a good correlation between the predictive empirical equation (1) and the experimental data, as use of equation (1) for this particular system suggests that the optimum number of Angiopep ligands is 20-30, and the optimum number of PMPC ligands is 400-600 (at room temperature, 25° C.). For this particular system, the key parameters for application in equation (1) are as follows:

PMPC Parameters:
[P]=2 nM
R=50 nm
d=10 nm
N(PEO)=10
Density PEO=0.5 nm$^2$
Density Glycocalyx=5 nm$^2$
$\delta_P$=0.6
$\delta_G$=0.2
$K_D$(PMPC)=5×10$^{-8}$ M
<SRB1> density=34 um$^{-2}$ for brain endothelial cells
<SRB1> density=24 um$^{-2}$ for sentinel cells (leukocytes)

Angiopep Parameters:
[P]=2 nM
R=50 nm
d=10 nm
N(PEO)=10
Density PEO=0.5 nm$^2$
Density Glycocalyx=5 nm$^2$
$\delta_P$=0.65
$\delta_G$=0.95
$K_D$(Angiopep)=3.13×10$^{-7}$ M
<LRP1> density=14 um$^{-2}$ for brain endothelial cells
<LRP1> density=28 um$^{-2}$ for sentinel cells (leukocytes)

A calculation of the steric potential $E_s$ as a function of polymersome radius R and the insertion parameters $\delta_G$ and $\delta_P$ is shown in FIG. 6. FIG. 6a shows a polymersome decorated with several Angiopep ligands, and FIG. 6b shows a polymersome decorated with PMPC chains. FIG. 6c shows the two ligands combined together. In all three scenarios the EP polymersomes interact with LRP1 (FIG. 6d) and/or SRB1 receptors (FIG. 6e) dispersed in the glycocalyx of the brain endothelial cells, which includes syndecan 4, a glycoprotein comprising four heparan sulfate chains with a polymerisation degree of 100. The steric interference, $U_{steric}$, exerted on LRP1 inserting into the polyethylene oxide brush on the polymersome and the steric interference, $U_{steric}$, exerted on the polymersome inserting into the glycocalyx are mathematically modelled in FIGS. 6f and 6g respectively, as a function of R and $\delta_P$ or $\delta_G$. $E_s$ is the sum of $U_{steric}$ exerted on LRP1 inserting into the PEO brush and $U_{steric}$ exerted on the polymersome inserting into the glycocalyx.

Interestingly, the experimental results demonstrate that the two ligands act synergistically allowing targeting using ligand numbers that alone will not correspond to any interactions. These lower limits to the effective ligand numbers are also predicted accurately by the empirical equation (1). This validates the ligand multiplexing strategy as a highly effective way to design nanoparticles or microparticles for targeted drug delivery.

Example 3: Binding of Polymersomes to Antigen Presenting Cells

Here we exemplify the incorporation of targeting ligands for targeting APC cells with applications in anti-cancer vaccines.

Figure 7:
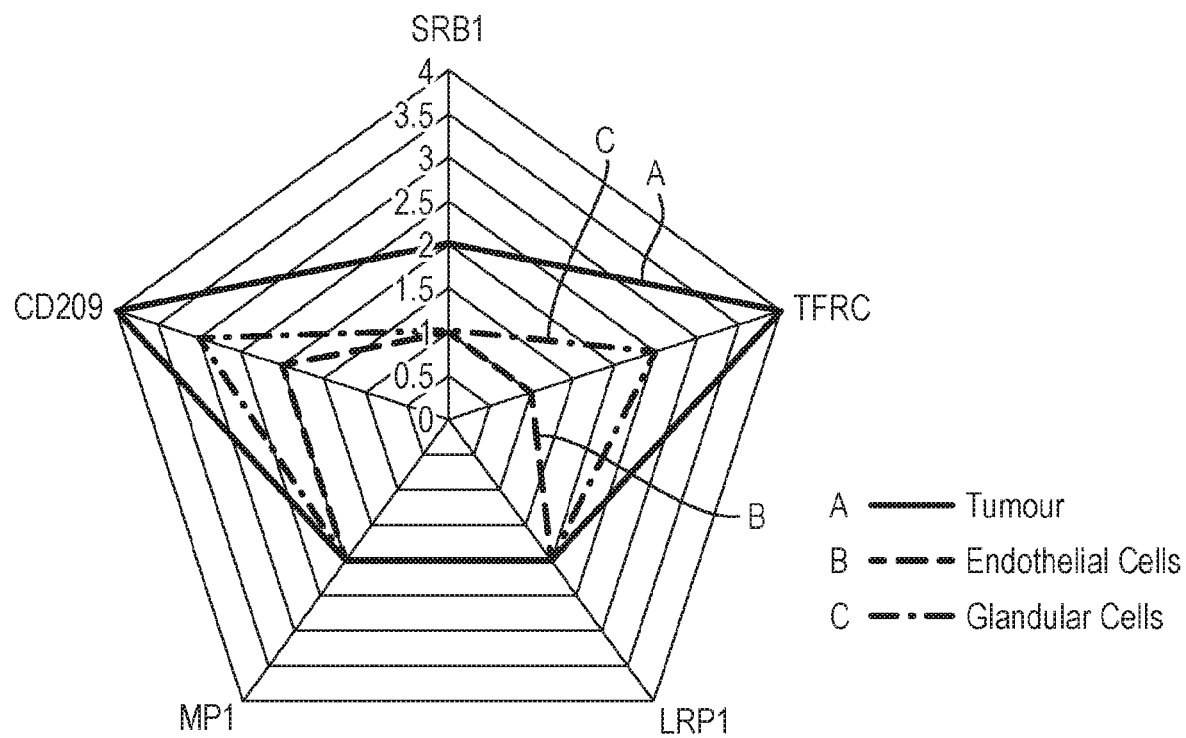
FIG. 7: Targeting of antigen presenting cells. Spider plot showing the expression of SRB1, TFRC, LRP1, and Mannose receptors in healthy tissues and in tumour tissue.

A bioinformatic search has been carried out using data from the human protein atlas to cross-matching receptors expressed in antigen presenting cells. The results are illustrated in the spider plot of FIG. 7, showing the expression of scavenger receptor B1 (SRB1), Transferrin (TFRC), lipoprotein receptor-related protein 1 (LRP1), and Mannose receptors in healthy tissues and in tumour tissue. The data show that only tumour tissues have three receptors all expressed at high levels, while healthy tissues express at high level only one or two receptors.

These receptors will be targeted using clinically-approved ligands attached on the surface of the polymersomes, to create the desired super-selectivity effect.

Example 4: Binding of Polymersomes to Neutrophils

Figure 8:
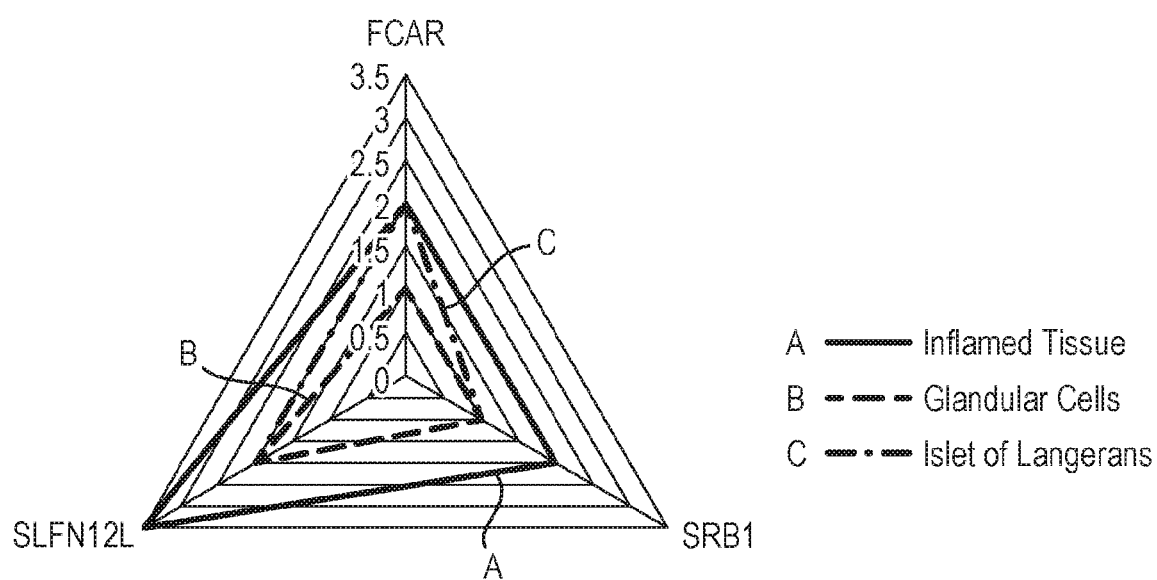
FIG. 8: Targeting of neutrophils. Spider plot showing the expression of SRB1, FCAR, and SLFN12L receptors in healthy and inflamed tissue.

A bioinformatic search has been carried out using data from the human protein atlas to cross-matching receptors expressed in antigen presenting cells. FIG. 8 illustrates a spider plot which shows the expression of SRB1, FCAR, and SLFN12L receptors in healthy and inflamed tissue. The data show particularly high levels of expression of SRB1 and SLFN12L in the inflamed tissue.

These receptors will be targeted using clinically-approved ligands attached on the surface of the polymersomes to create the desired super-selectivity effect.

Example 5: Binding of Polymersomes to Tumour Cells

Peritoneal carcinomatosis (PC) is a metastatic invasion of tumour cells into the lining within the abdominal cavity and the intra-abdominal organs. PC is a rare primary tumour and occurs in 60% of gastric, 40% of ovarian and 35% of colon malignancies. Median survival is 1 to 3 months. It is proposed to treat tumours with a balanced combination of chemotherapy and immune-modulation followed by priming the immune system with a "find and kill-me" signal to attack tumour metastasis.

Figure 9:
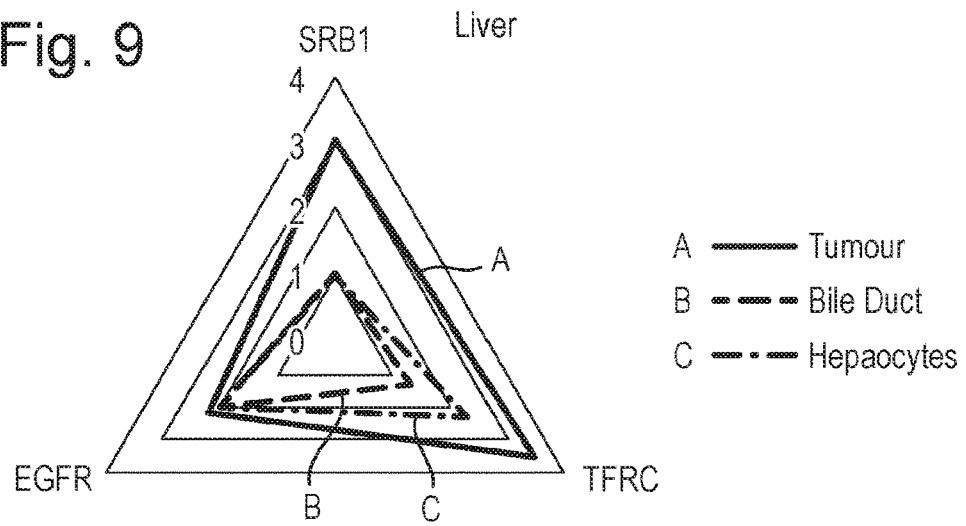
FIG. 9: Targeting of tumour cells. Spider plots showing the expression of SRB1, EGFR and TFRC receptors in healthy liver (top), colorectal (middle) and the female genital (bottom) alongside three different cancers associated liver (top), colorectal (middle) and the female genital (bottom). Note only the tumour tissues show all three receptors expressed at a medium/high level, whilst in the healthy tissues only either one or two receptor types are expressed at medium level.
Figure 9:
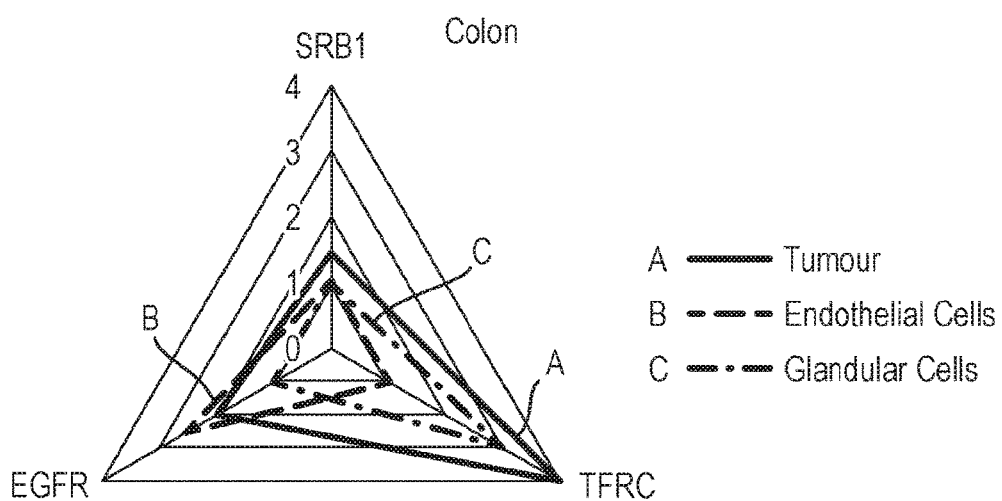
Figure 9:
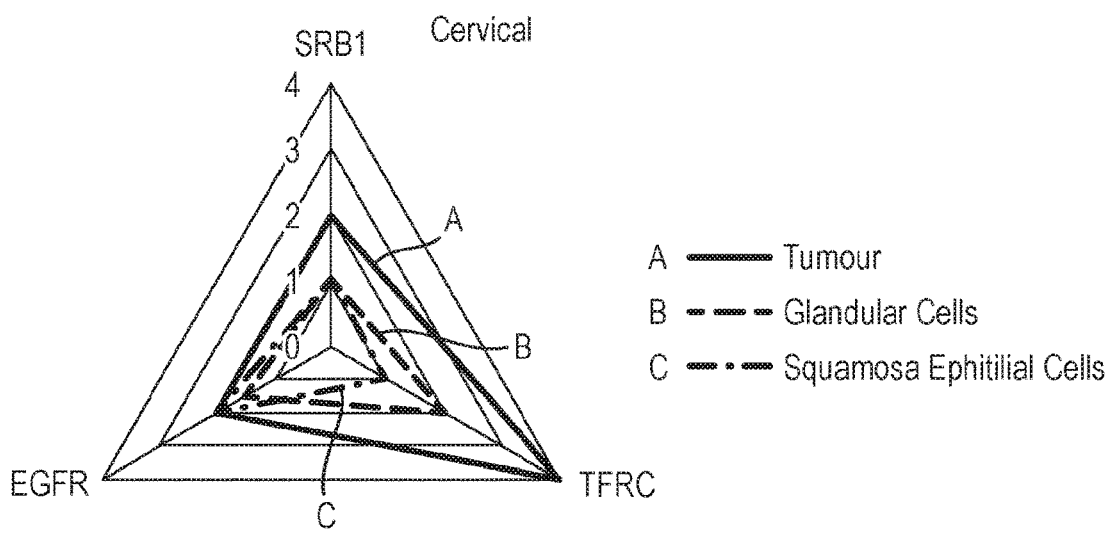

Three different receptors have been identified that in combination are over-expressed by tumour tissues, scavenger receptor B1 (SRB1), transferrin (TFRC) and epidermal growth factor (EGFR). The spider plots in FIG. 9 show the expression of these receptors in healthy peritoneal tissues (liver, colon, and female genital) and in the three most common PC associated tumours, gastric, colorectal and ovary. The data show that only tumour tissues have the three receptors all expressed at high levels, while healthy tissues express at high level only one or two receptors.

These receptors will be targeted using clinically-approved ligands attached on the surface of the particles of the invention (polyNauts particles) to create the desired super-selectivity effect. These are poly(2-methacryloyloxyethyl phosphorylcholine) (PMPC) for SRB1, Folic acid for FOLR1, and cetuximab for EGFR. PMPC is approved for the coating of STENTs, contact lens and catheters and it has been used in the clinical for a decade. Folic acid, also known as vitamin B9, is a common FDA-approved food supplement as well as a ligand used in several anticancer therapies. Finally, cetuximab is a monoclonal antibody approved for the treatment of colon cancer with wild-type KRAS, and is under clinical evaluation for several other malignancies.

Example 6: Binding of Polymersomes to Glioma Cells

Poor and inefficient drug delivery is a major reason for therapeutic failure in childhood brain tumours. The integrity of the blood-brain barrier (BBB) may render some paediatric tumours (e.g. diffuse midline gliomas) totally resistant to drug therapy, where the BBB (e.g. medulloblastoma and ependymoma) is partially disrupted this is also true. High doses of systemic chemotherapy are also required which result in significant and dose limiting side-effects. Therefore, improving drug transport across the BBB in a tumour specific manner could potentially result in both improved survival and also reduce systemic toxicity.

Figure 10A:
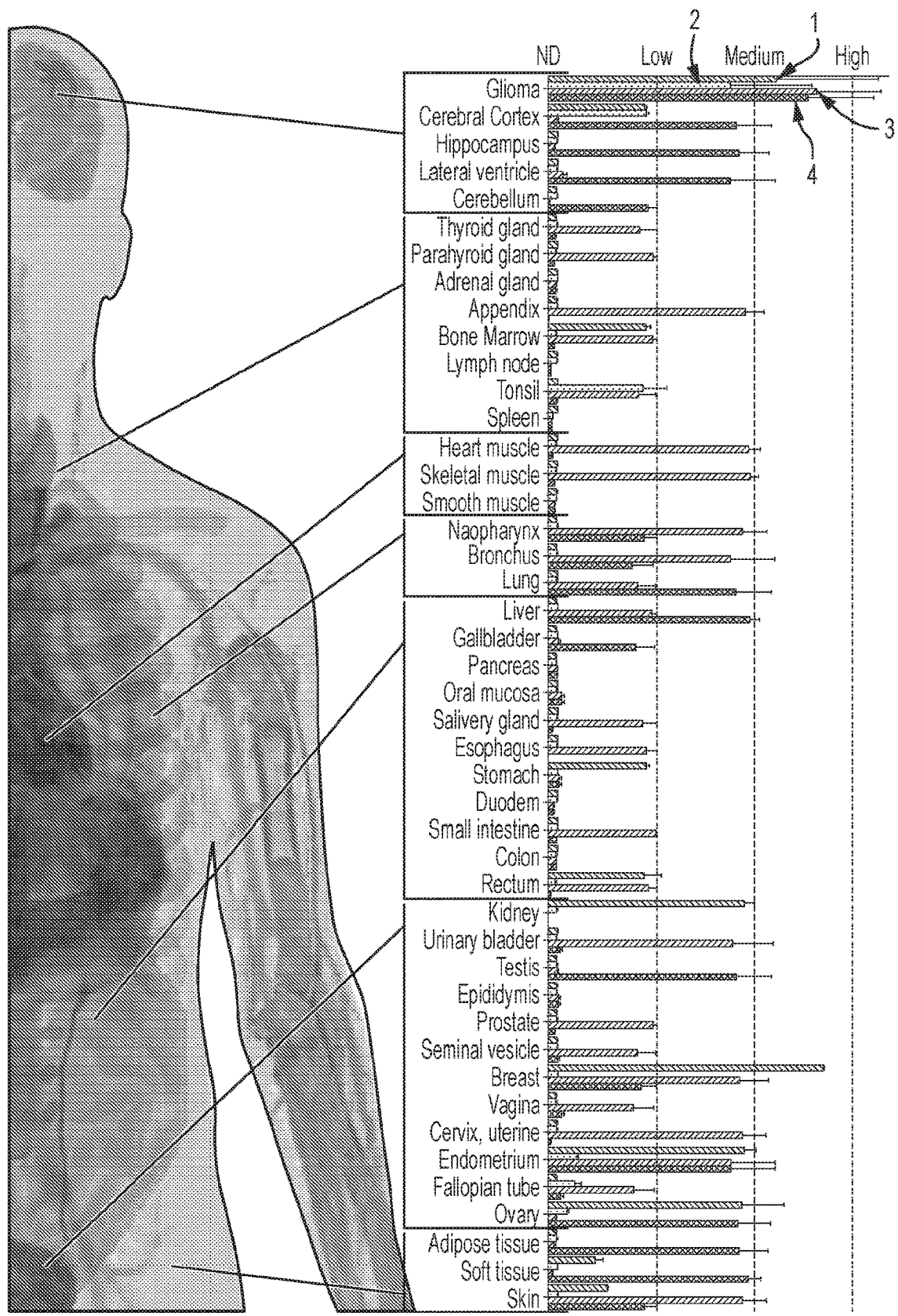
FIGS. 10a-10c: Whole body (FIG. 10a) and somatic brain and endothelia (FIG. 10b) expression levels of LRP-1, GLUT1, EGFR, and PDGFR-α receptors. These can be used to generate a super-selective spider plot (FIG. 10c) showing the receptor density combinations to achieve targeting of only BEC and Glioma cells.
Figure 10B:
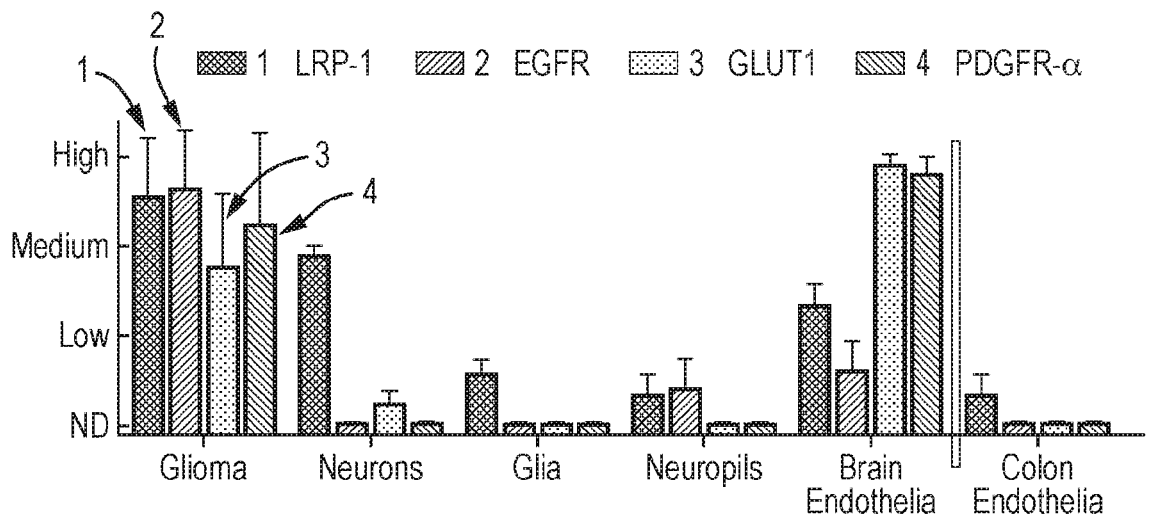
Figure 10C:
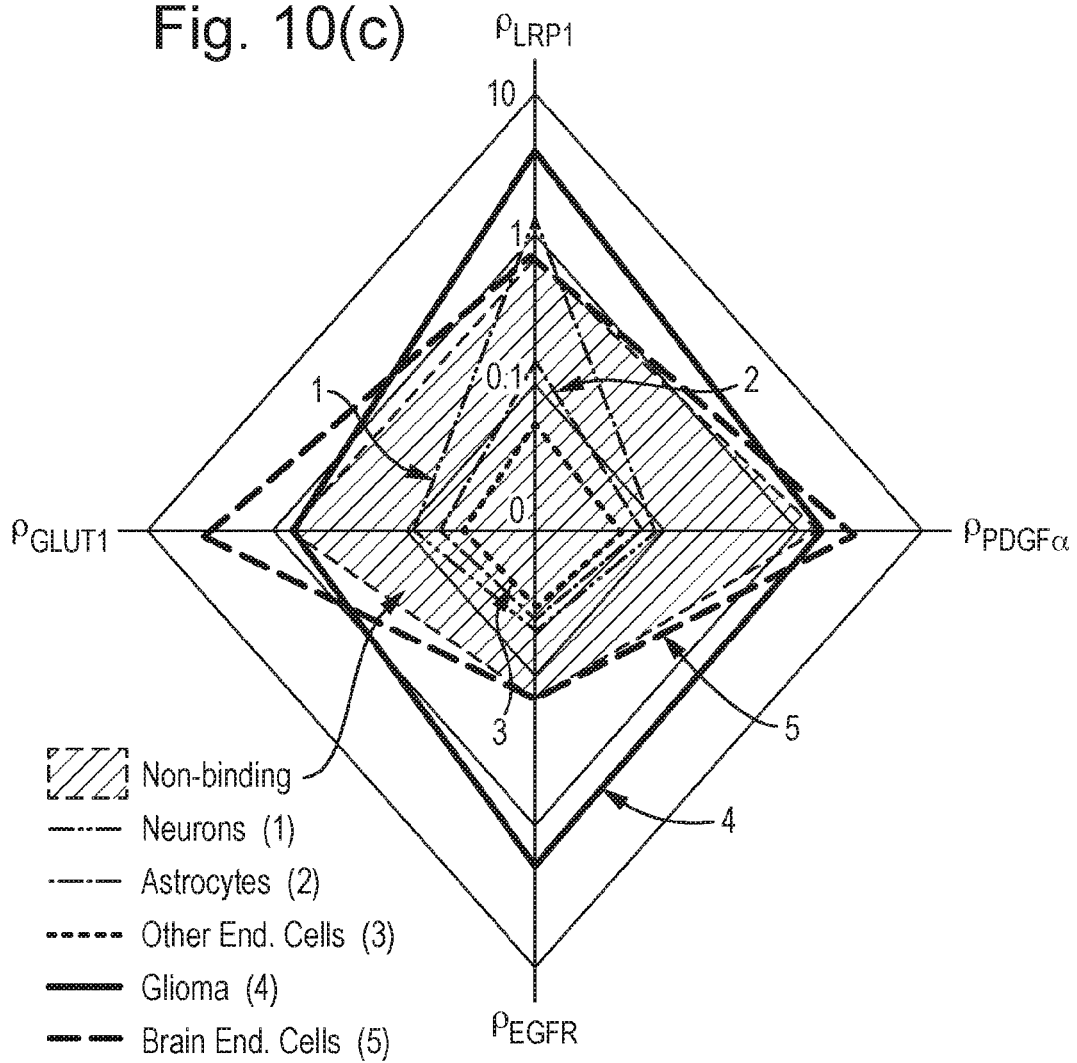

The challenge of creating a targeted formulation that both crosses the BBB and enters brain tumours limits the choice of potential receptors. A bioinformatic search has been carried out using data from the human protein atlas to cross-matching receptors both expressed at high level in brain endothelial and glioma cells and that are not expressed together in other tissue. The data shown in FIGS. 10a and 10b establish that the BBB marker low density lipoprotein receptor-related protein 1 (LRP1) and glucose transporters (GLUT1) are also expressed in glioma cells. The LRP1 matches the expression level of an established adult cancer associated marker, the epidermal growth factor receptor (EGFR). Similarly, paediatric tumour marker platelet-derived growth factor receptor alpha (PDGFR-α) is expressed at high levels in BEC. These data suggest that it will be possible to create the necessary binding profile to target both class of cells only. As shown in the spider plot in FIG. 10c this data can, through the super-selective design, lead to the tuning of the correct ligand composition onto the polymersome surface (using the empirical model described by equation (1)) to achieve selective targeting of these cells.

Example 7: Determination of Optimum Number of Ligands on a Polymersome Surface

Figure 11:
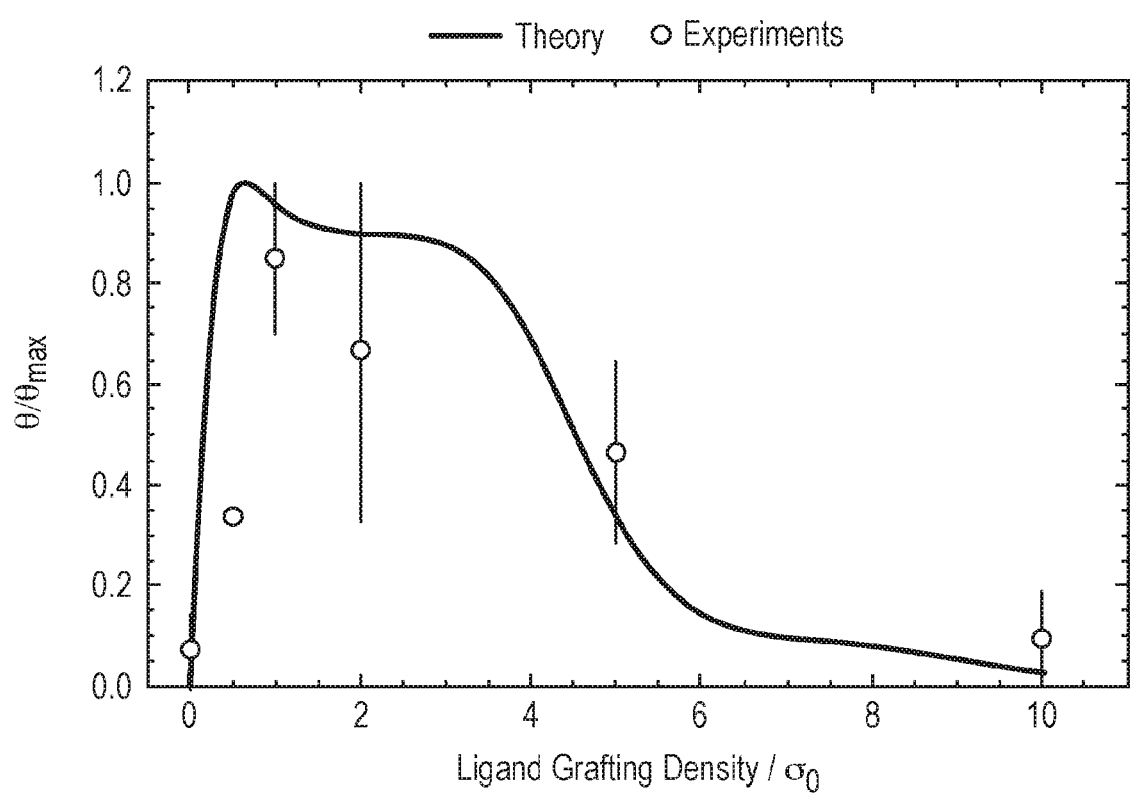
FIG. 11: Adsorption probability as a function of ligand number; comparison of theory vs experimental data. The theoretical curve has been calculated using the equation (2) described in Example 7, using a (double) Poisson average over both the number of receptors and on the number of ligands, whose average value (for the grafting density $\sigma_0=1$) was used as a fitting parameter. Error bars were calculated as an average over three independent measurements.

An experiment was carried out to determine the effect of density of Angiopep-2 ligands on a polymersome surface on the degree of adsorption to target cells. The results of this experiment were compared with the trend predicted by a theoretical model, and are shown in FIG. 11.

A. Theoretical Model

As shown previously (see, e.g., Martinez-Veracoeachea and Frenkel, *PNAS*, 2011, 108(27), 10963-10968, and Angioletti-Urberti, *Phys Rev Lett*, 2017, 118(6):068001), the adsorption probability θ for nanoparticle binding to a cell surface can be described via a Langmuir-type expression:

$$\theta = \left\langle \frac{zq(N_L, N_R, \Delta G)}{1 + zq(N_L, N_R, \Delta G)} \right\rangle_{N_x} \quad (2)$$

where $N_{x=L,R}$ is the number of ligands and receptors, respectively, and $\Delta G$ is the bond free energy (throughout this example, energies are always considered to be scaled by the thermal energy $k_B T$, where $k_B$ is Boltzmann's constant and T temperature). $\langle \ \rangle$ indicates an average over a Poisson distribution. This average is taken to account for inhomogeneities in the spatial distribution of receptors and/or ligands, which can be related either to the grafting procedure or to binders mobility on the surface. z is the nanoparticles' activity in the bulk solution, which for homogeneously-coated nanoparticles and dilute solutions can be taken equal to their number density (see Martinez-Veracoeachea and Frenkel, *PNAS*, 2011, 108(27), 10963-10968).

The central parameter in equation (2) is q, the partition function of the nanoparticle in the bound state, which depends on the number of ligands and receptors available for binding, as well as on the strength of their bond. This partition function can be written as $q=v_{bind}\exp(-F_{tot})$, where $v_{bind}=\pi(R_{np})^2 L$ is the binding volume of the absorption site, where $R_{np}$ is the size of the nanoparticle and L the range of distances at which the particle can bind, which can be approximated to the gyration radius of the ligand's tether. $F_{tot}$ is the free energy of adsorption, and is equal to the sum of $F_{att}$ (the attractive contribution generated by the formation of ligand-receptor bonds) and $F_{rep}$ (the repulsive contribution due to the steric repulsions between different components of the nanoparticles and target cells within the crowded environment of the binding region, e.g. receptor interactions with the polymer brush on the nanoparticle surface, and ligand interactions with the cell glycocalyx).

Assuming that the attractive contribution $F_{att}$ to the free energy of adsorption of a polymersome to its target receptor is dominated by bond formation between ligands and receptors, we can write:

$$F_{att} = -\ln \sum_\phi \Omega(\phi)\exp(-N_\phi \Delta G), \quad (3)$$

where the sum is over all configurations φ with $N_\varphi$ number of bonds. $\Delta G$ is the energy of a single bond (which depends on the specific ligand-receptor pair chosen) and $\Omega(\varphi)$ is the number of configurations with a specific number of bonds. In order to calculate this quantity, a specific binding scenario must be chosen. Different binding scenarios differ by the number of allowed configurations $\Omega(\varphi)$ (which measures the avidity entropy via $S=k_B\ln(\Omega)$. The weakest possible binding contribution is for "indifferent binding" (as described in Kitov and Bundle, *J Am Chem Soc*, 2003, 125(52), 16271-16284). In this case, only a single ligand can be bound to a receptor at any one time and we have $\Omega(\varphi)=N_R N_L$, where $N_R$ is the number of receptors on the cell surface and $N_L$ is the number of ligands on the polymersome surface, and $N_\varphi=1$, leading to $F_{att}=-\ln(N_R)-\ln(N_L)+\Delta G$. For the case of radial binding instead all ligands can bind to all receptors (but in each configuration only a single ligand can be bound to any specific receptor and vice versa), leading to:

$$\Omega_\phi = \Omega(N_\phi) = \binom{N_L}{N_\phi}\binom{N_R}{N_\phi}N_\phi! \quad (4)$$

and the sum in (3) extends from 0 to $\min(N_L,N_R)$. This partition function cannot be written in close form and it is not computationally efficient to calculate it with brute force. However, as shown by Angioletti-Uberti et al. (*J Chem Phys*, 2013, 138, 21102-21106), the ligand-receptor-mediated energy in any possible binding scenario (bar the case where the number of both ligands and receptors are 1 at the same time; see Tito and Angioletti-Uberti, *J Chem Phys*, 2016, 144(16), 161101), thus including the radial case, can be approximated to within a fraction of $k_B T$ accuracy by the set of coupled equations:

$$F_{att} = \sum_i N_i\left(\ln p_i + \frac{1-p_i}{2}\right) \quad (5)$$

$$p_i + \sum_j p_i p_j \chi = 1, \quad (6)$$

where $\chi=\exp(-\Delta G)$ can be interpreted as the single-bond strength (see Angioletti-Uberti, *Phys Rev Lett*, 2017, 118(6): 068001), which increases for lower values of $\Delta G$. In (6), the index i refers to any ligand or receptor in the system and the sum is extended over all binding partners j of i. Hence, there are $N_L+N_R$ coupled equations to solve. In the radial binding scenario one has that each ligand or receptor has the same number of neighbours (either $N_R$ for ligands or $N_L$ for receptors) and thus the previous equations reduce to two coupled equations only:

$$\begin{cases} p_L + N_R p_L p_R \chi = 1 \\ p_R + N_L p_L p_R \chi = 1 \end{cases}$$

whose simultaneous solution leads to $$F_{att} = \sum_{i=L,R} N_i \left( \ln p_i + \frac{1-p_i}{2} \right) \quad (7)$$

$$p_L = \frac{(N_L - N_R)\chi - 1 + \sqrt{4N_R\chi + (1 + (N_L - N_R)\chi)^2}}{2N_L\chi} \quad (8)$$

(and a symmetric formula changing the pedices L,R for $p_R$), which are used to plot the curve in FIG. 11 for a radial binding scenario.

As for $F_{rep}$, a model can be built by combining previous results by Halperin (*Langmuir*, 1999, 15(7), 2525-2533) and Zhulina (*Eur Phys J E: Soft Matter Biol Phys*, 2006, 20(3), 243-256 and *Macromolecules*, 2012, 45(11), 4429-4440) to calculate the repulsive free energy to insert an object in a polymer brush on a curved surface. Within this model, the following can be derived:

$$F_{rep} = A(z)N_R \quad (9)$$

$$A(z) = \quad (10)$$

$$V_R \left[ \sigma \left( 1 + \delta(z) \right) \left[ \left( 1 + \frac{(\gamma+2)N}{3R} \left( \frac{va^2}{3\sigma} \right)^{\frac{1}{\gamma+2}} \right)^{\frac{3}{\gamma+2}} - 1 \right]^{\gamma-1} \right]^{-\frac{1}{2}} (1 - \delta(z)^2)^{\frac{2}{4}}$$

where $V_R$ is the volume of the receptor, a the average area per polymer chain, $\delta=(z/h_0) \in [0,1]$ the distance between the nanoparticle and that of the surface scaled by the average brush height $h_0 = N(v_a^2/3\sigma)^{1/3}$ when grafted on a planar surface, N the degree of polymerisation, $v=a^3$ the volume of a monomer of size a and finally $\gamma$ is a parameter that depends on the radius of the nanoparticle core R with respect to the brush height, and is $\gamma=3$ for $h_0/R > (\sqrt{3}-1)$ and $\gamma=(1+h_0/R)^2$ otherwise.

B. Fitting of Experimental Data

The theoretical curve in FIG. 4 has been obtained by fitting the experimental data using the expression in equations (2) to (10) above, where a double Poisson average was taken over both the number of receptors per site as well as the number of interacting ligands, to take into account inhomogeneities in the functionalisation of the polymersomes. For calculating the attractive contribution, a radial binding scenario was assumed. The binding distance L was approximated to be the most probably end-to-end distance for the tether used to graft the ligand to the nanoparticle, which if treated as a Gaussian chain gives $L=2R_G=6$ nm for the test experimental system (see below). Further, $R=R_{np}+h$, $h=8$ nm, being the height of the brush, as estimated from the degree of polymerisation of the protective PEO coating and its grafting density using the Zhulina model (see *Eur Phys J E: Soft Matter Biol Phys*, 2006, 20(3), 243-256) and $R_{np}=50$ nm being the size of the nanoparticle as experimentally determined via Dynamic Light Scattering and cryoTEM experiments.

These numbers also give $\delta=0.75$ in (10) and $\gamma=(1+h_0/R)$ for the estimation of the repulsive contribution due to receptors via (10), for which $V_P=188$ nm$^3$ for the Angiopep receptor, as estimated from known structural data (see Xiaohe Tian et al., 2019, *Sci Adv*). This leaves three fitting parameters: the reference grafting density of ligands on the surface $\sigma_L$ (as only the ratio of the number of ligands between different polymersomes is known, not their absolute value; see below); the average grafting density of receptors and the repulsive contribution per ligand, for which, similarly to (9), the simple expression $F_{rep}=AN_L$ applies, where A contains all the compounded effects of unknown parameters describing the cell glycocalyx as well as all excluded volume interactions between ligands and the cell surface. Given these formulas, the experimental data can be fitted using a Monte Carlo annealing to minimise the quantity $$E = \Sigma_i \omega_i (\theta'_{i,exp} - \theta'_{i,theory})^2 / \Sigma_i \omega_i,$$

where $w_i$ can be taken as the inverse of the m.s.r.d. of each experimental data $\theta_{i,exp}$, the experimentally measured adsorption normalised by its maximum value among all polymersomes of different grafting densities. The procedure started with an effective temperature of 1, scaling the temperature by a factor of 0.95 every 100 MC sweeps until the temperature reaches a value of $10^{-7}$, at which point the system has already ceased to evolve. The overall procedure produced fitting parameters of $\sigma_L = 1.88 \cdot 10^{-3}/\text{nm}^2$ or around 7 interacting ligands within the polymersome area (for the reference polymersome) in contact with the binding site, $\sigma_R = 4.3 \times 10^{-5}/\text{nm}^2$, or an average 0.32 receptors per adsorption site, and a repulsive parameter of $A=0.62 \ k_B T$.

C. Preparation of Polymersomes

PEO-b-PDPA and $N_3$—PEO-b-PDPA copolymers were synthesised as previously reported by the atom-transfer radical polymerisation method (see Blanazs et al., *Adv Functional Mat*, 2009, 19(18), 2906-2914 and Gaitzsch et al., *Polymer Chem*, 2016, 7(17), 3046-3055). For fluorescent labelling ($Cy_5$-$PEG_{113}$-$PDPA_{100}$) and ligand conjugation (Angiopep$_2$-$PEG_{68}$-$PDPA_{90}$) one eq. of $N_3$-PEO-b-PDPA was first assembled in PBS by pH switch procedure (as described in Contini et al., *IScience*, 2018, 7, 132-144). The solution of self-assembled polymer was then degassed by sonication and inert gas flow under stirring. The degassed solution was mixed with 1.2 eq. of the corresponding ligand. For peptide conjugation (AP-alkyne), the peptide was dissolved in degassed PBS pH 7.4, whereas water insoluble ligands such as $Cy_5$-alkyne was added in degassed dimethylsulfoxide (DMSO) having a final DMSO:PBS ratio of 10:1. Then sodium ascorbate (5 eq.) was added and the mixture was further degassed for at least 30 min. Finally, 1 eq. of $CuSO_4$ was added under inert atmosphere and the reaction was left reacting at 40° C. for 72 hours protected from light. Dialysis of the labelled polymers was done against DMSO and then water to purify them (MWCO at least 5 KDa for peptide purification and 3.5 KD for dyes purification). The labelled polymers were recovered after lyophilisation. To prepare polymersomes with increasing amount of ligand, the co-polymer $PEG_{113}$-$PDPA_{80}$ was mixed with Angiopep$_2$-$PEG_{68}$-$PDPA_{90}$ (0-10 mol %) and $Cy_5$-$PEG_{113}$-$PDPA_{100}$ (10 mol %) and the mixtures were dissolved in tetrahydrofuran:dimethyl sulfoxide (90:10) at a final total polymer concentration of 20 mg/mL. 2.3 mL of PBS pH 7.4 (aqueous phase) were pumped at 2 L/min into the organic solutions using an automated syringe pump. The addition of the aqueous phase was carried out under continuous stirring at 40° C. After the injection, an additional extra volume of PBS (pH 7.4) (3.7 mL) was added manually. In order to remove the remaining organic solvent, the polymersomes solutions were transferred in a cellulose semipermeable membrane (3.5 kDa cut-off) and dialysed in PBS (pH 7.4) for over 24 hours at room temperature. The samples were centrifuged at 1000 r.c.f. for 10 min, sonicated at 4° C. for 20 min and purified through a size exclusion chromatography (SEC) column packed with Sepharose 4B. All the samples were stored at 4° C. and protected from light until further use. Polymersomes average sizes and morphology were characterised by Dynamic Light Scattering (DLS) and Transmission Electron Microscopy (TEM). DLS measurements were performed using a Malvern Zeta sizer equipped with an He-Ne 4 mW 633 nm laser, diluting the polymersomes solution with PBS (pH 7.4) in disposable polystyrene cuvettes. For TEM analysis, polymersomes were deposited for 1 min on glow-discharged carbon-coated copper grids and then stained with a PTA solution at 0.5% (w/v) for 2 s.

D. Measurement of Adsorption Probability

FaDu cells (ATCC HTB-43) were seeded on an 8-well chamber slide (iBidi) at a density of 20,000 cells per well and maintained in MEME (Minimum Essential Medium Eagle M5650-Sigma) supplemented with 10% Fetal Bovine Serum and 1% penicillin/streptomycin at 37° C. in 5% $CO_2$. After 24 hours, the media was removed, cells were washed 3 times with Dulbecco's Phosphate-Buffered Saline (DPBS) and fixed with 3.7% of paraformaldehyde (v/v in DPBS) for 10 min at room temperature. Fixed cells were incubated for 1 h at 37° C. with $Cy_5$-labelled- and Angiopep$_2$-decorated polymersomes (0.15 mg/mL) in PBS (pH 7.4). After 1 hour, polymersomes solutions were removed, cells were washed 3 times with DPBS and treated for 5 min at room temperature with CellMask Green (1:1000 in DPBS). Cells were left in Live Imaging Solution and the adsorption of polymersomes on cell membranes was analysed on a Leica SP8 confocal laser scanning microscope with 63X oil immersion lens. The total emission fluorescence of $Cy_5$-labelled polymersomes was measured in the 650-700 nm range using an excitation wavelength of 633 nm and collected using a z stack of 30 images. Image data were acquired on 50 cells for each percentage of Angiopep$_2$ studied and processed using ImageJ software. All the experiments were performed in triplicate.

The invention claimed is:

1. A polymersome for selective binding to the surface of a brain endothelial cell, wherein the polymersome comprises at least a first ligand type on its external surface and at least a second ligand type on its external surface, wherein said first ligand type is Angiopep-2 and is capable of binding to low density lipoprotein receptor-related protein 1 (LRP-1) on said cell surface, and said second ligand type is poly(2-(methacryloyloxy)ethyl phosphorylcholine) and is capable of binding to scavenger receptor class B, member 1 (SCARB1), further wherein the polymersome comprises from 10 to 30 Angiopep-2 ligands and from 200 to 800 poly(2-(methacryloyloxy)ethyl phosphorylcholine) ligands, or from 20 to 30 Angiopep-2 ligands and from 50 to 800 poly(2-(methacryloyloxy)ethyl phosphorylcholine) ligands, and wherein the polymersome comprises, on its external surface, a polymer brush comprising poly(ethylene glycol) (PEG) or poly(oligo(ethylene glycol) methyl ether methacrylate) (POEGMA), and wherein the polymersome has a diameter of from 50 to 150 nm.

2. A polymersome according to claim 1, wherein the polymersome comprises from 20 to 30 Angiopep-2 ligands.

3. A polymersome according to claim 1, wherein the polymersome comprises from 400 to 600 poly(2-(methacryloyloxy)ethyl phosphorylcholine) ligands.

4. A polymersome according to claim 1, further comprising a drug encapsulated within the polymersome.

5. A polymersome according to claim 4, wherein the drug is selected from a neuroprotectant, an immunomodulatory drug, a non-steroidal anti-inflammatory drug (NSAID), a corticosteroid, a disease-modifying antirheumatic drug (DMARD), an immunosuppressant, a TNF-alpha inhibitor and an anti-cancer drug.

6. A pharmaceutical composition comprising a plurality of the polymersomes according to claim 1, and one or more pharmaceutically acceptable excipients or diluents.

7. A polymersome for selective binding to the surface of a brain endothelial cell, wherein the polymersome comprises at least a first ligand type on its external surface and at least a second ligand type on its external surface, wherein said first ligand type is Angiopep-2 and said second ligand type is poly(2-(methacryloyloxy)ethyl phosphorylcholine), further wherein the polymersome comprises from 20 to 30 Angiopep-2 ligands and from 400 to 600 poly(2-(methacryloyloxy)ethyl phosphorylcholine) ligands, wherein the polymersome comprises, on its external surface, a polymer brush comprising poly(oligo(ethylene glycol) methyl ether methacrylate) (POEGMA), and wherein the polymersome has a diameter of from 50 to 150 nm.

\* \* \* \* \*

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: Angiopep-2

<400> SEQUENCE: 1

Thr Phe Phe Tyr Gly Gly Ser Arg Gly Lys Arg Asn Asn Phe Lys Thr
1               5                   10                  15

Glu Glu Tyr

<210> SEQ ID NO 2
<211> LENGTH: 12
<212> TYPE: PRT
<213> ORGANISM: Artificial Sequence
<220> FEATURE:
<223> OTHER INFORMATION: EGFR ligand

<400> SEQUENCE: 2

Tyr His Trp Tyr Gly Tyr Thr Pro Gln Asn Val Ile
1               5                   10
```